United States Patent [19]
Andy et al.

[11] Patent Number: 5,268,453
[45] Date of Patent: Dec. 7, 1993

[54] TISSUE-SELECTIVE INSULIN ANALOGS

[75] Inventors: Robin J. Andy, Cupertino, Calif.; Eric R. Larson, Mystic, Conn.

[73] Assignee: Scios Inc., Mountain View, CA; Pfizer Inc., New York, N.Y.

[21] Appl. No.: 918,953

[22] Filed: Jul. 30, 1992

Related U.S. Application Data

[63] Continuation-in-part of Ser. No. 741,938, Aug. 8, 1991.

[51] Int. Cl.$^5$ .................. C07K 7/00; A61K 37/26; C12P 21/06
[52] U.S. Cl. ................................. 530/303; 435/69.4
[58] Field of Search .................. 530/303; 435/69.4

[56] References Cited

FOREIGN PATENT DOCUMENTS 9012814 11/1990 World Int. Prop. O. .

OTHER PUBLICATIONS

Podlecki et al. 1983 Diabetes 32:697.
Tompkins et al. 1981 Drabetologia 20:94–101.

Primary Examiner—Robert J. Hill, Jr.
Assistant Examiner—K. Cochrane Carlson
Attorney, Agent, or Firm—Morrison & Foerster

[57] ABSTRACT

Human insulin analogs are disclosed. These analogs are tissue-selective. Accordingly, pharmaceutical formulations containing the analogs of the invention provide superior clinical benefits as compared to human insulin when used in the treatment of patients suffering from diabetes. The analogs are modified at amino residue A12, A15 or A19, are different from the naturally occurring residue at said position, and are hepatoselective. Also disclosed are human insulin analogs modified at amino acid residues A12 or A14 or amino acid residues A10 and A13 different from naturally occurring residues or residues at said position or positions and are peripheral selective. DNA sequences and microorganisms comprising sequences coding for human insulin analogs are also provided. Processes for preparing the human insulin analogs are described.

12 Claims, 5 Drawing Sheets

1

```
          10         20         30         40         50         60
CCGGGGTTCT ATGTTTGTGA ACCAACACCT GTGCGGATCC CACCTGGTGG AAGCTCTCTA
          70         80         90
CCTAGTGTGC GGGGAACGAG GCTTCTTCTA CACACCC
```

3

```
          10         20         30         40         50         60
AAGACCCGCC GGGAGGCAGA GGACCTGCAG GTGGGGCAGG TGGAGCTGGG CGGGGGCCCT
          70         80         90
GGTGCAGGCA GCCTGCAGCC CTTGGCCCTG GAGGGGTCC
```

5

```
          10         20         30         40         50         60
CTGCAGAAGC GTGGCATTGT GGAACAATGC TGTACCAGTA TCTGCTCCCT CTACCAGCTG
          70
GAGAACTACT GCAACTAGA
```

6

```
          10         20         30         40         50         60
AGCTTCTAGT TGCAGTAGTT CTCCAGCTGG TAGAGGGAGC AGATACTGGT ACAGCATTGT
          70         80         90
TCCACAATGC CACGCTTCTG CAGGGACCCC TCCAG
```

4

```
          10         20         30         40         50         60
GGCCAAGGGC TGCAGGCTGC CTGCACCAGG GCCCCCGCCC AGCTCCACCT GCCCCACCTG
          70         80         90
CAGGTCCTCT GCCTCCCGGC GGGTCTTGGG TGTGTAGAA
```

2

```
          10         20         30         40         50         60
GAAGCCTCGT TCCCCGCACA CTAGGTAGAG AGCTTCCACC AGGTGGGATC CGCACAGGTG
          70         80
TTGGTTCACA AACATAGAAC CCCGGGTAC
```

FIG. I

CAT

```
           24                                              48
ATG GAG AAA AAA ATC ACT GGA TAT ACC ACC GTT GAT ATA TCC CAA TGG
Met Glu Lys Lys Ile Thr Gly Tyr Thr Thr Val Asp Ile Ser Gln Trp 72                                              96
CAT CGT AAA GAA CAT TTT GAG GCA TTT CAG TCA GTT GCT CAA TGT ACC
His Arg Lys Glu His Phe Glu Ala Phe Gln Ser Val Ala Gln Cys Thr 120                                             144
TAT AAC CAG ACC GTT CAG CTG GAT ATT ACG GCC TTT TTA AAG ACC GTA
Tyr Asn Gln Thr Val Gln Leu Asp Ile Thr Ala Phe Leu Lys Thr Val 168                                             192
AAG AAA AAT AAG CAC AAG TTT TAT CCG GCC TTT ATT CAC ATT CTT GCC
Lys Lys Asn Lys His Lys Phe Tyr Pro Ala Phe Ile His Ile Leu Ala
```

LINKER
```
           216                                             240
CGC CTG ATG AAT GCT CAT CCG GAA TTC GAG CTC GGT ACC CGG GGT TCT
Arg Leu Met Asn Ala His Pro Glu Phe Glu Leu Gly Thr Arg Gly Ser
```

B chain
```
           264                                             288
ATG TTT GTG AAC CAA CAC CTG TGT GGA TCC CAC CTG GTG GAA GCT CTC
Met Phe Val Asn Gln His Leu Cys Gly Ser His Leu Val Glu Ala Leu 312                                             336
TAC CTA GTG TGC GGG GAA CGA GGC TTC TTC TAC ACA CCC AAG ACC CGC
Tyr Leu Val Cys Gly Glu Arg Gly Phe Phe Tyr Thr Pro Lys Thr Arg
```

C-peptide
```
           360                                             384
CGG GAG GCA GAG GAC CTG CAG GTG GGG CAG GTG GAG CTG GGC GGG GGC
Arg Glu Ala Glu Asp Leu Gln Val Gly Gln Val Glu Leu Gly Gly Gly 408                                             432
CCT GGT GCA GGC AGC CTG CAG CCC TTG GCC CTG GAG GGG TCC CTG CAG
Pro Gly Ala Gly Ser Leu Gln Pro Leu Ala Leu Glu Gly Ser Leu Gln
```

A-chain
```
           456                                             480
AAG CGT GGC ATT GTG GAA CAA TGC TGT ACC AGC ATC TGC TCC CTC TAC
Lys Arg Gly Ile Val Glu Gln Cys Cys Thr Ser Ile Cys Ser Leu Tyr CAG CTG GAG AAC TAC TGC AAC TAG AAG CTT
Gln Leu Glu Asn Tyr Cys Asn aaa Lys Leu
```

FIG. 2a

INSULIN

```
       ┌─oligo 1                                                        48
       TC CGG GGT TCT ATG TTT AAA CAA CAC CTG TGC ACG GGA TCC CAC
       CA TGG CCA AGA TAC ATG TTT GTT GTG GAC ACG CCT AGG GTG
       └─oligo 2   Met Phe Lys Gln His Leu Cys Thr Gly Ser His
                                                                        96
       CTG GTG GAA GCT CTC TAC CTA GTG TGC GGG GAA CGA GGC TTC TTC TAC
       GAC CAC CTT CGA GAG ATG GAT CAC ACG CCC CTT GCT CCG AAG AAG ATG
       Leu Val Glu Ala Leu Tyr Leu Val Cys Gly Glu Arg Gly Phe Phe Tyr┘└─oligo 4
             ┌─oligo 3                                                  144
       ACA CCC AAG ACC CGC CGG GAG GAC CTG CAG GTG GGG CAG GTG
       TGT GGG TTC TGG GCG GCC CTC CTG GAC GTC CAC CCC GTC CAC
       Thr Pro Lys Thr Arg Arg Glu Asp Leu Gln Val Gly Gln Val
                                                                        192
       GAG CTG GGC GGG GGC CCT GGT GCA GGC AGC CTG CAG CCC TTG GCC CTG
       CTC GAC CCG CCC CCG GGA CCA CGT CCG TCG GAC GTC GGG AAC CGG GAC
       Glu Leu Gly Gly Gly Pro Gly Ala Gly Ser Leu Gln Pro Leu Ala Leu└─oligo 6
                  ┌─oligo 5                                             240
       GAG GGG TCC CTG CAG AAG CGT GCA ATT GTG GAA CAA TGC ACC TGT AGT
       CTC CCC AGG GAC GTC TTC GCA CGT TAA CAC CTT GTT ACG TGG ACA TCA
       Glu Gly Ser Leu Gln Lys Arg Ala Ile Val Glu Gln Cys Thr Cys Ser
                                                                        264
       ATC TGC TCC CTC TAC CAG CTG GAG AAC TAC TGC AAC TAG A
       TAG ACG AGG GAG ATG GTC GAC CTC TTG ATG ACG TTG ATC TTC GA
       Ile Cys Ser Leu Tyr Gln Leu Glu Asn Tyr Cys Asn End
```

FIG. 2b

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
( A ) LENGTH: 97 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:1:

CCGGGGTTCT ATGTTTGTGA ACCAACACCT GTGCGGATCC CACCTGGTGG AAGCTCTCTA 60

CCTAGTGTGC GGGGAACGAG GCTTCTTCTA CACACCC 97

( 2 ) INFORMATION FOR SEQ ID NO:2:

( i ) SEQUENCE CHARACTERISTICS:
( A ) LENGTH: 89 base pairs
( B ) TYPE: nucleic acid ( C ) STRANDEDNESS: single
( D ) TOPOLOGY: linear ( i i ) MOLECULE TYPE: DNA ( x i ) SEQUENCE DESCRIPTION: SEQ ID NO:2:

GAAGCCTCGT TCCCCGCACA CTAGGTAGAG AGCTTCCACC AGGTGGGATC CGCACAGGTG  60

TTGGTTCACA AACATAGAAC CCCGGGTAC  89

( 2 ) INFORMATION FOR SEQ ID NO:3:

( i ) SEQUENCE CHARACTERISTICS:
( A ) LENGTH: 99 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:3:

AAGACCCGCC GGGAGGCAGA GGACCTGCAG GTGGGGCAGG TGGAGCTGGG CGGGGGCCCT  60

GGTGCAGGCA GCCTGCAGCC CTTGGCCCTG GAGGGGTCC  99

( 2 ) INFORMATION FOR SEQ ID NO:4:

( i ) SEQUENCE CHARACTERISTICS:
( A ) LENGTH: 99 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:4:

GGCCAAGGGC TGCAGGCTGC CTGCACCAGG GCCCCCGCCC AGCTCCACCT GCCCCACCTG  60

CAGGTCCTCT GCCTCCCGGC GGGTCTTGGG TGTGTAGAA  99

( 2 ) INFORMATION FOR SEQ ID NO:5:

( i ) SEQUENCE CHARACTERISTICS:
( A ) LENGTH: 79 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:5:

CTGCAGAAGC GTGGCATTGT GGAACAATGC TGTACCAGTA TCTGCTCCCT CTACCAGCTG  60

GAGAACTACT GCAACTAGA  79

( 2 ) INFORMATION FOR SEQ ID NO:6:

( i ) SEQUENCE CHARACTERISTICS:
( A ) LENGTH: 95 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:6:

AGCTTCTAGT TGCAGTAGTT CTCCAGCTGG TAGAGGGAGC AGATACTGGT ACAGCATTGT  60

TCCACAATGC CACGCTTCTG CAGGGACCCC TCCAG  95

( 2 ) INFORMATION FOR SEQ ID NO:7:

( i ) SEQUENCE CHARACTERISTICS:
    ( A ) LENGTH: 510 base pairs
    ( B ) TYPE: nucleic acid
    ( C ) STRANDEDNESS: double
    ( D ) TOPOLOGY: linear ( i i ) MOLECULE TYPE: cDNA ( i x ) FEATURE:
    ( A ) NAME/KEY: CDS
    ( B ) LOCATION: 1..510
    ( D ) OTHER INFORMATION:

( x i ) SEQUENCE DESCRIPTION: SEQ ID NO:7:

| | | | | | | | | | | | | | | | | |
|---|---|---|---|---|---|---|---|---|---|---|---|---|---|---|---|---|
| ATG | GAG | AAA | AAA | ATC | ACT | GGA | TAT | ACC | ACC | GTT | GAT | ATA | TCC | CAA | TGG | 48 |
| Met | Glu | Lys | Lys | Ile | Thr | Gly | Tyr | Thr | Thr | Val | Asp | Ile | Ser | Gln | Trp | |
| 1 | | | | 5 | | | | | 10 | | | | | 15 | | |
| CAT | CGT | AAA | GAA | CAT | TTT | GAG | GCA | TTT | CAG | TCA | GTT | GCT | CAA | TGT | ACC | 96 |
| His | Arg | Lys | Glu | His | Phe | Glu | Ala | Phe | Gln | Ser | Val | Ala | Gln | Cys | Thr | |
| | | | 20 | | | | | 25 | | | | | 30 | | | |
| TAT | AAC | CAG | ACC | GTT | CAG | CTG | GAT | ATT | ACG | GCC | TTT | TTA | AAG | ACC | GTA | 144 |
| Tyr | Asn | Gln | Thr | Val | Gln | Leu | Asp | Ile | Thr | Ala | Phe | Leu | Lys | Thr | Val | |
| | | 35 | | | | | 40 | | | | | 45 | | | | |
| AAG | AAA | AAT | AAG | CAC | AAG | TTT | TAT | CCG | GCC | TTT | ATT | CAC | ATT | CTT | GCC | 192 |
| Lys | Lys | Asn | Lys | His | Lys | Phe | Tyr | Pro | Ala | Phe | Ile | His | Ile | Leu | Ala | |
| | 50 | | | | | 55 | | | | | 60 | | | | | |
| CGC | CTG | ATG | AAT | GCT | CAT | CCG | GAA | TTC | GAG | CTC | GGT | ACC | CGG | GGT | TCT | 240 |
| Arg | Leu | Met | Asn | Ala | His | Pro | Glu | Phe | Glu | Leu | Gly | Thr | Arg | Gly | Ser | |
| 65 | | | | | 70 | | | | | 75 | | | | | 80 | |
| ATG | TTT | GTG | AAC | CAA | CAC | CTG | TGT | GGA | TCC | CAC | CTG | GTG | GAA | GCT | CTC | 288 |
| Met | Phe | Val | Asn | Gln | His | Leu | Cys | Gly | Ser | His | Leu | Val | Glu | Ala | Leu | |
| | | | | 85 | | | | | 90 | | | | | 95 | | |
| TAC | CTA | GTG | TGC | GGG | GAA | CGA | GGC | TTC | TTC | TAC | ACA | CCC | AAG | ACC | CGC | 336 |
| Tyr | Leu | Val | Cys | Gly | Glu | Arg | Gly | Phe | Phe | Tyr | Thr | Pro | Lys | Thr | Arg | |
| | | | 100 | | | | | 105 | | | | | 110 | | | |
| CGG | GAG | GCA | GAG | GAC | CTG | CAG | GTG | GGG | CAG | GTG | GAG | CTG | GGC | GGG | GGC | 384 |
| Arg | Glu | Ala | Glu | Asp | Leu | Gln | Val | Gly | Gln | Val | Glu | Leu | Gly | Gly | Gly | |
| | | 115 | | | | | 120 | | | | | 125 | | | | |
| CCT | GGT | GCA | GGC | AGC | CTG | CAG | CCC | TTG | GCC | CTG | GAG | GGG | TCC | CTG | CAG | 432 |
| Pro | Gly | Ala | Gly | Ser | Leu | Gln | Pro | Leu | Ala | Leu | Glu | Gly | Ser | Leu | Gln | |
| | 130 | | | | | 135 | | | | | 140 | | | | | |
| AAG | CGT | GGC | ATT | GTG | GAA | CAA | TGC | TGT | ACC | AGC | ATC | TGC | TCC | CTC | TAC | 480 |
| Lys | Arg | Gly | Ile | Val | Glu | Gln | Cys | Cys | Thr | Ser | Ile | Cys | Ser | Leu | Tyr | |
| 145 | | | | | 150 | | | | | 155 | | | | | 160 | |
| CAG | CTG | GAG | AAC | TAC | TGC | AAC | TAG | AAG | CTT | | | | | | | 510 |
| Gln | Leu | Glu | Asn | Tyr | Cys | Asn | | | | | | | | | | |
| | | | | 165 | | 167 | | | | | | | | | | |

( 2 ) INFORMATION FOR SEQ ID NO:8:

( i ) SEQUENCE CHARACTERISTICS:
    ( A ) LENGTH: 167 amino acids
    ( B ) TYPE: amino acid
    ( D ) TOPOLOGY: linear ( i i ) MOLECULE TYPE: protein ( x i ) SEQUENCE DESCRIPTION: SEQ ID NO:8:

| | | | | | | | | | | | | | | | |
|---|---|---|---|---|---|---|---|---|---|---|---|---|---|---|---|
| Met | Glu | Lys | Lys | Ile | Thr | Gly | Tyr | Thr | Thr | Val | Asp | Ile | Ser | Gln | Trp |
| 1 | | | | 5 | | | | | 10 | | | | | 15 | |
| His | Arg | Lys | Glu | His | Phe | Glu | Ala | Phe | Gln | Ser | Val | Ala | Gln | Cys | Thr |
| | | | 20 | | | | | 25 | | | | | 30 | | |
| Tyr | Asn | Gln | Thr | Val | Gln | Leu | Asp | Ile | Thr | Ala | Phe | Leu | Lys | Thr | Val |
| | | 35 | | | | | 40 | | | | | 45 | | | |
| Lys | Lys | Asn | Lys | His | Lys | Phe | Tyr | Pro | Ala | Phe | Ile | His | Ile | Leu | Ala |
| | 50 | | | | | 55 | | | | | 60 | | | | |

```
Arg  Leu  Met  Asn  Ala  His  Pro  Glu  Phe  Glu  Leu  Gly  Thr  Arg  Gly  Ser
 65                  70                  75                            80

Met  Phe  Val  Asn  Gln  His  Leu  Cys  Gly  Ser  His  Leu  Val  Glu  Ala  Leu
                    85                       90                       95

Tyr  Leu  Val  Cys  Gly  Glu  Arg  Gly  Phe  Phe  Tyr  Thr  Pro  Lys  Thr  Arg
               100                      105                      110

Arg  Glu  Ala  Glu  Asp  Leu  Gln  Val  Gly  Gln  Val  Glu  Leu  Gly  Gly  Gly
          115                      120                      125

Pro  Gly  Ala  Gly  Ser  Leu  Gln  Pro  Leu  Ala  Leu  Glu  Gly  Ser  Leu  Gln
     130                      135                      140

Lys  Arg  Gly  Ile  Val  Glu  Gln  Cys  Cys  Thr  Ser  Ile  Cys  Ser  Leu  Tyr
145                      150                      155                      160

Gln  Leu  Glu  Asn  Tyr  Cys  Asn
               165       167
```

( 2 ) INFORMATION FOR SEQ ID NO:9:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:9:

CCGGAATTCG AGCTCGGTAC CCGG                                              24

( 2 ) INFORMATION FOR SEQ ID NO:10:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:10:

GCCAAGCTTC TAGTTGCAGT AGTTCTCCAG CTGGTAGAGA CCGCA                       45

( 2 ) INFORMATION FOR SEQ ID NO:11:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:11:

GCCAAGCTTC TAGTTGCAAT GGTTTTC                                           27

( 2 ) INFORMATION FOR SEQ ID NO:12:

( i ) SEQUENCE CHARACTERISTICS:
        ( A ) LENGTH: 275 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 209..271
        ( D ) OTHER INFORMATION: /note="The insulin analog is numbered from amino acid number 1 of the
A chain."

( x i ) SEQUENCE DESCRIPTION: SEQ ID NO:12:

CCGGGGTTCT ATGTTTGTGA ACCAACACCT GTGCGGATCC CACCTGGTGG AAGCTCTCTA 60

CCTAGTGTGC GGGGAACGAG GCTTCTTCTA CACACCCAAG ACCCGCCGGG AGGCAGAGGA 120

CCTGCAGGTG GGGCAGGTGG AGCTGGGCGG GGGCCCTGGT GCAGGCAGCC TGCAGCCCTT 180

GGCCCTGGAG GGGTCCCTGC AGAAGCGT GGC ATT GTG GAA CAA TGC TGT ACC      232
                                Gly Ile Val Glu Gln Cys Cys Thr
                                 1                   5

AGT ATC TGC GGT CTC TAC CAG CTG GAG AAC TAC TGC AAC TAGA            275
Ser Ile Cys Gly Leu Tyr Gln Leu Glu Asn Tyr Cys Asn
    10                  15                  20

( 2 ) INFORMATION FOR SEQ ID NO:13:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( x i ) SEQUENCE DESCRIPTION: SEQ ID NO:13:

Gly Ile Val Glu Gln Cys Cys Thr Ser Ile Cys Gly Leu Tyr Gln Leu
 1                   5                  10                  15

Glu Asn Tyr Cys Asn
                20

( 2 ) INFORMATION FOR SEQ ID NO:14:

( i ) SEQUENCE CHARACTERISTICS:
        ( A ) LENGTH: 275 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 209..271
        ( D ) OTHER INFORMATION: /note="The insulin analog
            is numbered from amino acid number 1 of the
            A chain."

( x i ) SEQUENCE DESCRIPTION: SEQ ID NO:14:

CCGGGGTTCT ATGTTTGTGA ACCAACACCT GTGCGGATCC CACCTGGTGG AAGCTCTCTA 60

CCTAGTGTGC GGGGAACGAG GCTTCTTCTA CACACCCAAG ACCCGCCGGG AGGCAGAGGA 120

CCTGCAGGTG GGGCAGGTGG AGCTGGGCGG GGGCCCTGGT GCAGGCAGCC TGCAGCCCTT 180

GGCCCTGGAG GGGTCCCTGC AGAAGCGT GGC ATT GTG GAA CAA TGC TGT ACC      232
                                Gly Ile Val Glu Gln Cys Cys Thr
                                 1                   5

AGT ATC TGC TCC CTC TAC CAG CTG GAG AAC CAT TGC AAC TAGA            275
Ser Ile Cys Ser Leu Tyr Gln Leu Glu Asn His Cys Asn
    10                  15                  20

( 2 ) INFORMATION FOR SEQ ID NO:15:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( x i ) SEQUENCE DESCRIPTION: SEQ ID NO:15:

Gly Ile Val Glu Gln Cys Cys Thr Ser Ile Cys Ser Leu Tyr Gln Leu
1               5                   10                  15

Glu Asn His Cys Asn
            20

( 2 ) INFORMATION FOR SEQ ID NO:16:

( i ) SEQUENCE CHARACTERISTICS:
        ( A ) LENGTH: 276 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 11..272

( x i ) SEQUENCE DESCRIPTION: SEQ ID NO:16:

```
CCGGGGTTCT ATG TTT GTG AAC CAA CAC CTG TGC GGA TCC CAC CTG GTG                49
           Met Phe Val Asn Gln His Leu Cys Gly Ser His Leu Val
           1               5                   10

GAA GCT CTC TAC CTA GTG TGC GGG GAA CGA GGC TTC TTC TAC ACA CCC                97
Glu Ala Leu Tyr Leu Val Cys Gly Glu Arg Gly Phe Phe Tyr Thr Pro
    15                  20                  25

AAG ACC CTG CCG GGA GGC AGA GGA CCT GCA GGT GGG GCA GGT GGA GCT               145
Lys Thr Leu Pro Gly Gly Arg Gly Pro Ala Gly Gly Ala Gly Gly Ala
30                  35                  40                  45

GGG CGG GGG CCC TGG TGC AGG CAG CCT GCA GCC CTT GGC CCT GGA GGG               193
Gly Arg Gly Pro Trp Cys Arg Gln Pro Ala Ala Leu Gly Pro Gly Gly
                50                  55                  60

GTC CCT GCA GAA GCG TGG CAT TGT GGA ACA ATG CTG TAC CAG TAT CTG               241
Val Pro Ala Glu Ala Trp His Cys Gly Thr Met Leu Tyr Gln Tyr Leu
            65                  70                  75

CTC CCT CTA CCA GCT GGA GAA CTA CTG CAA C TAGA                                276
Leu Pro Leu Pro Ala Gly Glu Leu Leu Gln
        80                  85
```

( 2 ) INFORMATION FOR SEQ ID NO:17:

( i ) SEQUENCE CHARACTERISTICS:
        ( A ) LENGTH: 87 amino acids
        ( B ) TYPE: amino acid
        ( D ) TOPOLOGY: linear ( i i ) MOLECULE TYPE: protein ( x i ) SEQUENCE DESCRIPTION: SEQ ID NO:17:

Met Phe Val Asn Gln His Leu Cys Gly Ser His Leu Val Glu Ala Leu
1               5                   10                  15

Tyr Leu Val Cys Gly Glu Arg Gly Phe Phe Tyr Thr Pro Lys Thr Leu
            20                  25                  30

Pro Gly Gly Arg Gly Pro Ala Gly Gly Ala Gly Gly Ala Gly Arg Gly
        35                  40                  45

Pro Trp Cys Arg Gln Pro Ala Ala Leu Gly Pro Gly Gly Val Pro Ala
    50                  55                  60

Glu Ala Trp His Cys Gly Thr Met Leu Tyr Gln Tyr Leu Leu Pro Leu
65                  70                  75                  80

Pro Ala Gly Glu Leu Leu Gln
            85

( 2 ) INFORMATION FOR SEQ ID NO:18:

( i ) SEQUENCE CHARACTERISTICS:
    ( A ) LENGTH: 276 base pairs
    ( B ) TYPE: nucleic acid
    ( C ) STRANDEDNESS: double
    ( D ) TOPOLOGY: linear ( x i ) SEQUENCE DESCRIPTION: SEQ ID NO:18:

```
AGATCAACGT CATCAAGAGG TCGACCATCT CCCTCGTCTA TGACCATGTC GTAACAAGGT      60
GTTACGGTGC GAAGACGTCC CTGGGGAGGT CCCGGTTCCC GACGTCCGAC GGACGTGGTC     120
CCGGGGGCGG GTCGAGGTGG ACGGGGTGGA CGTCCAGGAG ACGGAGGGCC GTCCCAGAAC     180
CCACACATCT TCTTCGGAGC AAGGGGCGTG TGATCCATCT CTCGAAGGTG GTCCACCCTA     240
GGCGTGTCCA CAACCAAGTG TTTGTATCTT GGGGCC                                276
```

TISSUE-SELECTIVE INSULIN ANALOGS

CROSS REFERENCES

This application is a continuation-in-part of our pending U.S. application Ser. No. 07/741,938 filed Aug. 8, 1991, which application is incorporated herein by reference in its entirety and to which application we claim priority under 35 USC §120.

FIELD OF THE INVENTION

The present invention relates generally to biologically active proteins and analogs thereof. More specifically, the invention relates to analogs of human insulin which analogs are tissue-selective and to pharmaceutical formulations containing such analogs and their use in the treatment of diabetes. DNA sequences and microorganisms comprising sequences coding for human insulin analogs are also provided. Processes for preparing the human insulin analogs are described.

BACKGROUND OF THE INVENTION

Insulin is a protein and more specifically a hormone that controls the metabolism of glucose. Lack of insulin within an animal results in the animal developing diabetes and excess amounts of insulin results in coma. Insulin is a polypeptide which is produced by the beta-cells of the islets of Langerhans of the pancreas. Pancreatic secretions of insulin are stimulated by high blood levels of glucose and amino acids after meals. Glucose uptake is then stimulated by the action of insulin on various tissues (e.g., muscles, liver, and fat). Insulin also stimulates glycogen and fat synthesis. Pharmaceutical preparations of insulin are used therapeutically in the treatment of diabetes mellitus known as type I and type II diabetes.

The inability of certain animals, such as humans, to generate sufficient amounts of insulin in the pancreas leads to the development of diabetes mellitus. Diabetes mellitus is a syndrome characterized by abnormal insulin secretion and various metabolic and vascular impairments. Individuals suffering from diabetes mellitus are currently treated by the administration of porcine, bovine or recombinant human insulin. The administration of insulin, however, does not consistently mimic the effects of endogenous insulin and may result in hypoglycemia and long-term complications such as atherosclerosis.

Animal derived insulin is not chemically identical to human insulin and sometimes contains other biologically active impurities. Efforts were made to develop a means of producing insulin which is chemically identical to human insulin and which does not include any biologically active impurities. As a result of such efforts, recombinant techniques have been developed to produce human insulin and proinsulin polypeptides in microorganisms which are isolated and purified for pharmaceutical use. For example, see European Patent Application No. 0 055 945, published 14 Jul. 1982, which application is incorporated herein by reference, for its disclosure of recombinant techniques and methodologies for producing insulin and proinsulin polypeptides and the isolation of such polypeptides.

As indicated above, present technology makes it possible to recombinantly produce insulin having an identical amino acid sequence to human proinsulin and/or insulin which can then be purified and used in pharmaceutical preparations. However, insulin has a plurality of functions. For example, it inhibits hepatic glucose production and stimulates peripheral glucose utilization thereby controlling the metabolism of glucose. Because of these different functions and because the site of administration of the exogenous insulin typically is different from the natural release site, when individuals suffering from diabetes are treated it may be desirable if the insulin which is administered inhibited hepatic glucose production to a greater degree compared with its ability to stimulate peripheral glucose utilization. The need for the insulin administered to act differently from natural insulin in order to obtain a more natural result is explained further below.

Insulin has an overall effect of lowering the glucose concentration in the bloodstream. This effect is obtained by the operation of insulin on two different types of tissue.

The glucose lowering effects of insulin occur in both hepatic and peripheral tissues in order to regulate glucose levels in blood. The interaction of insulin with hepatic receptors results in a decrease in glucose production by the liver as well as increased liver storage of glucose as glycogen; interaction with the peripheral receptors on fat and muscle cells results in an increase in glucose utilization. Both interactions result in a lowering of glucose concentration in the bloodstream. In both liver and peripheral cells, binding to the receptor is concomitant with insulin clearance from the system; i.e., as insulin is utilized, it is also cleared.

In the normal operation of endogenous insulin, the majority of the hormone secreted by the pancreas interacts with the hepatic receptors. This apparent preference is thought to be due to the proximity of the liver to the source of the hormone. Once released into the general circulation, most of the insulin appears to be utilized by peripheral cells, due to the large number of peripheral receptors available. One reason why the administration of insulin does not achieve the "natural" balance between hepatic and peripheral activity may be that the initial introduction of the drug into the general circulation system provides little opportunity for interaction with the hepatic receptors. However, a high degree of such interaction takes place when endogenous insulin is released from the pancreas.

Insulin is initially synthesized in the islets of Langerhans of the pancreas as the single chain peptide proinsulin. Proinsulin has 1-2% of the potency of native insulin when assayed in vitro, about 15% of the potency of insulin in vivo. and a circulating half-life of 30 min as compared to 4 min for insulin. Proinsulin is relatively hepatoselective in vivo (Glauber, H. S., et al., *Diabetes* (1986) 35:311-317; Peavy, D. E., et al., *J. Biol. Chem.* (1985) 260:13989-13994; Davis, S. N., et al., *Diabetes* (1988) 37:74 (abstract)). The in vivo hepatoselectivity of proinsulin is 50% more than that of insulin per se. However, proinsulin has too low a potency for most uses.

Insulin is thought to circulate predominantly as a monomer. The monomer is a disulfide-linked, two-chain molecule consisting of A chain of 21 amino acids and B chain of 30. The amino acid sequences of human, porcine and bovine insulin are well established. (The amino acid sequences of insulins of many other species have also been determined.) Attempts to discern which are the essential residues in these peptides were begun some time ago. By observing the conservation of residues between the insulins derived from various species, it was suggested that a largely invariable region on the surface of the monomer is the receptor binding region. This region includes A-chain residues A1 (Gly), A5 (Gln), A19 (Tyr), and A21 (Asn) as well as B chain residues B24 (Phe), B25 (phe), B26 (Tyr), B12 (Val), and B16 (Tyr).

de Meyts R. A. et al. *Nature* (1978) 273:504–509, tested 29 insulin-type molecules including animal insulins and proinsulins, insulin-like growth factors and chemically modified insulins for ability to bind to receptor and for biological potency. de Meyts et al. found a one thousand-fold variation over the series of 29 analogs wherein the essential residues were shown to be some of the 8 carboxyterminal residues of the B chain and the A21 (Asn) residue of the A chain.

Tompkins, C. B., et al., *Diabetologia* (1981) 20:94–101, showed that certain analogs stimulated hypoglycemia entirely by increasing peripheral glucose uptake, whereas others did so by decreasing hepatic glucose production. In these studies, A1, B29-diacetyl derivatives of insulin were able to stimulate peripheral glucose uptake, while A1-B29 cross-linked insulins and proinsulin decreased hepatic glucose production.

Later studies by Nakagawa, S. H., et al., *J. Biol. Chem* (1986) 261:7332–7341, confirmed the importance of the carboxy terminal region of the B chain. Studies of binding to the hepatocyte receptor showed that insulin residues B26-B30 could be deleted without decrease in binding or biological potency when the carboxyl group is alphacarboxamidated to preserve the hydrophobic character of the carboxy terminal B chain domain. However, deletion of residues B25-B30 or B24-B30 resulted in a decrease in potency.

A reduction in potency was also observed when the phenylalanine at B25 was replaced by leu or ser or by homophenylalanine; however, replacement by naphthyl-1-alanine or naphthyl-2-alanine at B25 decreased binding activity to a lesser extent. The decreased activity effected by replacement of Phe at B25 by Ala, Ser, Leu or homophenylalanine was reversible by deletion of the remaining carboxy-terminal residues B26-B30. The authors concluded that steric hindrance involving the carboxy-terminal domain of the B chain helped direct interaction of insulin with its receptor, that the negative effect of this domain is "reversed by filling of a site reflecting interaction of the receptor and the beta-aromatic ring of B25 (phe)" and that the remaining carboxy-terminal residues, besides B25, were important in effecting the interaction of this residue with the receptor. Further studies by this group (Nakagawa, S. H., et al., *J. Biol. Chem* (1987) 262:1254–1258) showed that the downstream residues must be deleted to reverse the effect of replacement of B25 (Phe) by ser and that replacement of residues B26 (Tyr) or B27 (Thr) does not reverse this decrease in affinity. It was further shown that cross-linking between B29 (Lys) and A1 (Gly) decreases the affinity of insulin for the receptor. These studies were directed to an effort to enhance the potency of insulin.

Coincidentally, however, a diabetic patient was shown to produce a mutant form of insulin having Leu instead of Phe at B25. Two other patients were shown to have mutations at the codons for B24 or B25, but the encoded insulin was not characterized (Shoelson, S., et al., *Nature* (1983) 302:540–543).

Increased binding to receptor and increased potency was shown to be a property of insulin iodinated at the tyrosine residue B26 (Podlecki, D. A., et al., Diabetes (1983) 32:697–704). Similarly, Schwartz, G. P., et al., *Proc. Natl. Acad. Sci. USA* (1987) 84:6408–6411, described a superactive insulin with enhanced binding both to hepatic and peripheral receptors which contains an aspartic acid substitution for the natural histidine at B10 of human insulin.

Still others have reported insulin analogs which have specified properties thought desirable. For example, Brange, J., et al., *Nature* (1988) 333:679–682, prepared analogs with substitutions at B9, B12, B10, B26, B27 and B28 which are designed to prevent formation of dimers.

International Patent Application WO 90/12814, published 1 November 1990, discloses hepatospecific insulin analogs wherein tryptophan or other bulky, hydrophobic residues selected from the group consisting of tryptophan, naphthylalanine, N-gamma-dansyl-alpha, gamma-diaminobutyric acid, leucine, valine, phenylalanine and other hydrophobic amino acids are substituted at the A13, A14, A15, A19 and B16 positions of the insulin polypeptide. The naturally occurring amino acids which are conventionally described as hydrophobic are alanine, valine, leucine, isoleucine, proline, methionine, phenylalanine and tryptophan, or alternatively amino acids whose side chains consist only of hydrocarbon, except for the sulfur atom of methionine and the nitrogen atom of tryptophan (J. Darnell, *Molecular Cell Biology*, Scientific American Books, New York, 1986). In contrast, the sidechains of histidine and glutamine are described as polar or hydrophilic groups.

Contrary to the teaching in WO 90/12814, the present invention provides the surprising and beneficial result that substitution by non-hydrophobic amino acids at A19 produces insulin analogs which are hepatoselective in vivo. Further, the present invention provides the surprising and beneficial result that substitution by phenylalanine at A14 produces analogs that are peripheral selective. Such A14 analogs have a different and distinct therapeutic use from the hepatospecific use disclosed in International Patent Application WO 90/12814.

The present invention recognizes the desirability of tissue selectivity when providing insulin to a patient from an exogenous source, i.e., not directly from the pancreas.

SUMMARY OF THE INVENTION

Purified human insulin analogs which are tissue selective are disclosed. By tissue selective is meant hepatoselective and peripheral selective insulin analogs. Hepatoselective analogs inhibit hepatic glucose production in vivo to a greater extent than they stimulate peripheral glucose utilization, as compared to normal human insulin activity when given by the same route of administration. Peripheral selective analogs inhibit hepatic glucose production in vivo to a lesser extent than they stimulate peripheral glucose utilization, as compared to normal human insulin activity when given by the same route of administration.

An object of the invention is to provide human insulin analogs comprising an amino acid residue at position A12 different from the naturally occurring residue at said position, wherein the analog is hepatoselective. In one embodiment of the invention, the human insulin analog comprises A12Gly.

Another object of the invention is to provide human insulin analogs comprising an amino acid residue at position A19 different from the naturally occurring residue at said position and which is not a hydrophobic residue, wherein the analog is hepatoselective. In one embodiment of the invention, the human insulin analog comprises A19His or A19Gln.

Another object of the invention is to provide human insulin analogs comprising an amino acid residue at position A12 different from the naturally occurring residue at said position, in combination with one or both of an amino acid residue at A19 different from the naturally occurring residue at said position and an amino acid residue at A15 different from the naturally occurring residue at said position, wherein the analog is hepatoselective. In one embodiment of the invention, a glycine residue may be substituted for the naturally occurring residue at the A12 position and a histidine residue may be substituted for the naturally occurring residue at the A19 position.

Another object of the invention is to provide human insulin analogs comprising an amino acid residue at position A12, or amino acid residues at position A10 and A13 in combination, wherein said residue or residues are different from the naturally occurring residue or residues at said position or positions and wherein the analog is peripheral selective. In one embodiment of the invention, an alanine residue may be substituted for the naturally occurring residue at the A12 position; or a proline residue may be substituted for the naturally occurring residue at the Al? position and a tryptophan may be substituted for the naturally occurring residue at the A13 position.

Yet another aspect of the invention is to provide a pharmaceutically effective amount of a peripheral selective human insulin analog which may be administered to an animal in need of peripheral selective insulin treatment, wherein the amino acid residue at position A14 is phenylalanine.

Accordingly, such tissue-selective analogs can be included, individually or in combination, within pharmaceutical formulations comprising a pharmaceutical excipient material and a pharmaceutically effective amount of a human insulin analog which can be administered in injectable, pump, or other forms to an individual in need thereof to effectively treat type I and type II diabetics.

Yet another object of the invention is to provide DNA sequences and microorganisms comprising sequences coding for human insulin analogs. Another object is to provide processes for preparing the human insulin analogs.

A primary object of the invention is to provide purified, chemically synthesized, or recombinant human insulin analogs.

An advantage of the present invention is that the insulin analogs can be formulated into pharmaceutical preparations which can effectively treat type I and type II diabetics.

Another advantage of the present invention is that it provides for a treatment regime for diabetics and other individuals which has superior clinical benefits as compared to treatment regimes using insulin formulations wherein the insulin is identical in structure to human insulin.

These and other objects, advantages, and features of the present invention will become apparent to those persons skilled in the art upon reading the details of the structure, synthesis, and usage as more fully set forth below, reference being made to the accompanying drawings.

BRIEF DESCRIPTION OF THE DRAWINGS

FIG. 1 and SEQ ID NOS:1–6 show a representation of the six chemically synthesized oligonucleotides that are combined in a specific sequence and comprise a gene that codes for human proinsulin.

FIG. 2a and SEQ ID NOS:7–8 are representations of the DNA sequence encoding amino acids 1–73 of CAT, an 8 amino acid acid linker sequence, and human proinsulin. Also shown is a representation of the deduced amino acid sequence encoding human proinsulin protein. The location of the oligonucleotides described in FIG. 1 used to construct the proinsulin cDNA is given in FIG. 2b SEQ ID Nos.:16–18.

DETAILED DESCRIPTION OF THE INVENTION

Figure 3A:
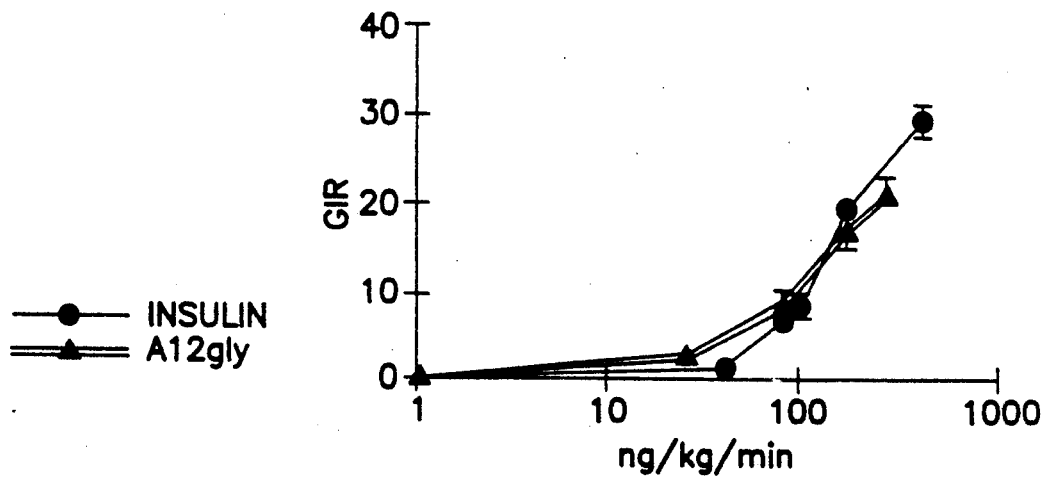
FIG. 3 shows glucose turnover in euglycemic, hyperinsulinemic clamps for insulin and the A12Gly analog. Graph A shows the rate of exogenous glucose infusion (GIR). Graph B shows the rate of glucose disappearance ($R_d$). Graph C shows the hepatic glucose output and is calculated as $R_a$ minus GIR. Under steady state conditions, $R_a = R_d$.

Before the present human insulin analogs, processes for making such and formulations containing and administering such are described, it is to be understood that this invention is not limited to the particular formulations and processes described, as such formulations and methodology may, of course, vary. It is also to be understood that the terminology used herein is for purposes of describing particular embodiments only, and is not intended to be limiting, since the scope of the present invention will be limited only by the appended claims.

It must be noted that as used in this specification and the appended claims, the singular forms "a," "an" and "the" include plural referents unless the context clearly dictates otherwise. Thus, for example, reference to "a formulation" includes mixtures of such formulations, reference to "an analog" includes mixtures of analogs, and reference to "the method of recombinant synthesis" includes one or more such methods of the type described herein, and so forth. The term human insulin analog, as used in the specification and appended claims, is not to be construed as implying that said analogs are necessarily derived directly or indirectly from a human source.

The present invention provides purified human insulin analogs which are tissue-selective. Hepatoselective insulin analogs have a greater activity at the liver than at the periphery when compared to the activity of insulin when given by the same route of administration. Accordingly, such tissue-selective analogs can be placed in pharmaceutical formulations and administered to diabetics to obtain superior clinical benefits as compared to human insulin. The amino acid sequence of each of the hepatoselective analogs of the invention is identical to the amino acid sequence of human insulin except at (a) position A12, wherein the amino acid residue is different from the naturally occurring residue at said position, or (b) position A19, wherein the amino acid residue is different from the naturally occurring residue at said position and is not hydrophobic, or (c) position A12 in combination with one or both of position A15 and position A19, wherein the amino acid residues at said positions are different from the naturally occurring residues at said positions and wherein the analog is hepatoselective. Additionally, various combinations of the A12, A15, and A19 amino acid substitutions are believed to result in hepatoselective insulin analogs.

The present invention further provides for human insulin analogs which are peripheral selective. Peripheral selective analogs inhibit hepatic glucose production in vivo to a lesser extent than they stimulate peripheral glucose utilization, as compared to normal human insulin activity when given by the same route of administration. Individuals who have a normal fasting glucose but impaired glucose tolerance may take advantage of the analogs of the present invention. For such individuals, a peripheral selective insulin analog may be used to stimulate peripheral activity of insulin to a greater extent when compared to activity of insulin at the liver. Such analogs can be incorporated into pharmaceutical formulations and administered to individuals to obtain superior clinical benefits as compared to human insulin. The amino acid sequence of each of the peripheral selective analogs of the invention is identical to the amino acid sequence of human insulin except at (a) position A12, wherein the amino acid residue is different from the naturally occurring residue at said position or (b) position A10, wherein the amino acid residue is different from the naturally occurring residue at said position and at position A13, wherein the amino acid residue is different from the naturally occurring residue at said position. The present invention may also be used to treat an animal in need of peripheral selective insulin treatment with a pharmaceutically effective amount of a human insulin analog, wherein the amino acid residue at A14 differs from the naturally occurring amino acid and is phenylalanine.

Any known method may be used to prepare insulin. For example, the cDNA coding for proinsulin can be constructed using oligonucleotides. Alternatively, the cDNA coding for proinsulin can be isolated from a human insulinoma cDNA library using an oligonucleotide screening probe. Isolation of a clone containing the sequence for proinsulin has been described previously by Bell, G. I., et al., *Nature* (1979) 282:525–527 and by Chan, S. J., et al., *Proc. Natl. Acad. Sci.* (1981) 78:5401–5405.

Both chemical synthesis and recombinant methods may be used to prepare the analogs of the invention. For recombinant material, it may be necessary to synthesize cDNAs, which is done by means known to those skilled in the art, such as, for example, by using PCR technology. When the appropriate cDNAs are constructed (e.g., by using DNA which encodes for proinsulin, making appropriate codon substitution and carrying out PCR), they are operably fused into expression plasmids, which plasmids are then used to transfect microorganism host cells such as *E. coli* bacteria. The transfected hosts are then allowed to grow and the constructed cDNAs will express the appropriate proinsulin analogs.

The expressed protein is subjected to standard isolation and purification procedures in order to obtain substantially pure polypeptides. The proinsulin analogs are preferably expressed as a CAT-analog fusion protein. Accordingly, after the transfected hosts are allowed to express the fusion protein, the fusion protein is isolated and then subjected to CNBr cleavage in order to separate the CAT from the desired proinsulin analog. The proinsulin analog undergoes sulfitolysis, is refolded, and undergoes enzymatic cleavage to produce the insulin analog. The insulin analog is then isolated and purified using protein purification procedures known to those skilled in the art. The resulting analogs are refolded polypeptides having the correct disulfide bonds so that the resulting structure has the desired biological activity. The analogs are purified to 95% or purer, preferably 99% or purer for use in patients.

Analogs of the invention can be tested in a euglycemic, hyperinsulinemic rat clamp using $^3$H-glucose as a tracer. In accordance with this technique, glucose is infused to maintain euglycemia. Insulin or an analog is also infused. Using $^3$H-glucose, glucose utilization by the periphery ($R_d$) and glucose production by the liver (HGO) can be calculated under steady state conditions using the equation of Steel et al., *Am. J. Physiol.* (1956) 187:15–24, incorporated herein by reference.

The purified analogs are formulated in injectable pharmaceutical formulations and administered in order to treat type I and type II diabetes. The amount of an insulin analog to be administered in a pharmaceutical composition is typically in the range of about 0.1 mg to about 10 mg per day.

Insulin analogs, for example, can be formulated into pharmaceutical compositions suitable for parenteral or nasal administration with appropriate excipients or carriers. Any of a variety of techniques known in the art can be used to prepare the pharmaceutical compositions. See, for example, *Remington's Pharmaceutical Sciences.* 17th Edition, Mack Publishing Company, Easton, Pa. (1985), which is incorporated herein by reference.

For example, the human insulin analogs described herein may be formulated in such a manner as to allow for their delivery by a variety of routes of administration, including, but not limited to intravenous injection, subcutaneous injection, and intramuscular injection. It is well recognized that insulins (e.g., human, bovine and porcine insulins) may be prepared in various formulations for subcutaneous or intramuscular injection, which, depending on the pH, zinc content, preservative, isotonic agent, buffer, and added basic proteins such as protamine, provide varied degrees of absorption when injected subcutaneously. See for example, Jens Brange, *Galenics of Insulin, The Physico-chemical Aspects of Insulin and Insulin Preparations,* Springer-Verlag, New York, 1987. Two general classes of formulation are particularly useful, and are known variably as "soluble, regular or rapid-acting" and protracted-acting derivatives. Such protracted-acting formulations fall into two subclasses: (1) "isophane," "NPH" or intermediate-acting and (2) "lente," "long-acting." Soluble formulations may be prepared in either acid or neutral form, but the neutral form may be better tolerated at the injection site, and also may reduce decomposition of the insulin analog on storage.

Crystalline zinc insulin analogs, suitable for use in pharmaceutical preparations may be prepared from a mixture containing approximately 1.5% of the insulin analog, 7% sodium chloride, 0.1 molar sodium acetate, and a quantity of zinc ions (from zinc chloride or zinc acetate) adequate to give a total of 0.8–0.9% of zinc by weight of the insulin analog, corresponding to approximately 4 zinc atoms per six molecules of the insulin analog. Adjustment of the pH of the solution by addition of a mineral acid, such as aqueous hydrochloric acid, to pH 5.5 or the isoelectric point of the analog if different from native insulin, causes crystals or an amorphous precipitate to form. This may be accelerated by addition of previously formed insulin analog crystals. on standing, the precipitate may gradually redissolve, and crystalline material forms, until a new equilibrium state is reached in which the crystalline form predominates. It is well known to those skilled in the art that addition of chemical compounds that interact either with zinc ions or the insulin molecules will change the crystallization pattern, and the optimal conditions for crystallization may change somewhat depending on the specific insulin analog. The crystalline form of the insulin analog so obtained may also be altered by addition of additives such as phenol or other hydroxylated aromatic compounds, as well as by substantial changes in the zinc content or the pH of the medium.

The crystalline insulin analogs may be used to prepare various formulations of the insulin analogs, which, depending on a number of factors, including added cationic organic compounds, such as globin, added basic proteins such as protamine, added zinc ion, or size or physical state of the insulin analog particles or crystals may have varied absorption rates from the site of injection, and hence varied onset and duration of action.

For example, a soluble, rapid acting form of the insulin analog for subcutaneous, intramuscular or intravenous injection may be prepared by dissolving the zinc insulin analog crystals in dilute hydrochloric acid at pH 3 to an insulin analog concentration of approximately 4%. After sterilization by filtration, additives for preservation of sterility, such as phenol (0.2%) or methylparaben (0.1%), isotonic agent (such as sodium chloride (0.7%) or glycerol (1.6%), buffering agent (such as sodium acetate 0.01M) may be added, such that their concentrations in the final formulation are approximately those shown in parentheses. The pH of the solution is adjusted carefully to neutrality (pH 7) with dilute alkali, such as 0.01 to 0.1N sodium hydroxide, in such a manner as to avoid attainment of locally high pH and degradation of the insulin analog. The neutral solution is then diluted with sterile water to the desired final insulin analog concentration, usually between 1 mg/mL and 10 mg/mL, and desired ionic strength, preferably isotonic with human serum, by addition of sterile water. Such a formulation may require storage at sub-ambient temperature, above 0° C., preferably at 4° C. to reduce degradation before use.

More protracted preparations, known as isophane formulations, may be prepared by addition of basic proteins, such as protamine (e.g., salmine), to a solution of insulin analog at neutral pH in equal (isophane) proportions. In the presence of added zinc ions approximately 0.2 μg of zinc ion per 25 mg of insulin analog), and a phenolic compound, either phenol or a cresol, a complex of the protamine and the insulin analog is formed as a precipitate, which has a more delayed absorption from the injection site than soluble insulin analog. It is well known to those skilled in the art, enabled by the disclosure herein, that the nature of the preparation so obtained, particularly the ratio of protamine and insulin analog in the precipitate, may be affected by modification of the pH, temperature, concentration of added zinc, and auxiliary substances. These variables may affect the absorption of insulin analog and hence onset and duration of action of the resulting formulation following subcutaneous or intramuscular injection.

An even more protracted-acting, or utralente formulation, may be obtained by increasing the amount of zinc present in the formulation. Such formulations may be prepared by adding zinc ions, from either zinc acetate or zinc chloride, to a suspension of crystalline insulin analog, such as that described in the preceding description for the preparation of insulin analog crystals, with the exception that phenol should be avoided. A final concentration of total zinc ion of approximately 0.09 to 0.15 mg/mL is desirable, depending on the final concentration of insulin analog in the formulation, the optimal amount being that which allows a concentration of approximately 0.05 mg/mL of free zinc ion in solution (not complexed to the insulin analog precipitate). It is known to those skilled in the art, enabled by the disclosure herein, that the size and variability of the crystals obtained in this manner may affect action of the resulting formulation following subcutaneous or intramuscular injection.

Another protracted form, or lente formulation, may be prepared by dissolving the free insulin analog at acid pH (e.g., pH 3 in dilute hydrochloric acid), such that the insulin analog concentration is in the range of 4% and, after sterile filtration, zinc is added (as zinc chloride or zinc acetate) such that a final zinc concentration of 0.09 to 0.15 mg/ml is obtained. The pH is then adjusted carefully to neutrality with dilute alkalai such that an amorphous precipitate forms. It is well known to those skilled in the art, enabled by the disclosure herein, that the nature of the precipitate so obtained may vary with the factors influencing the precipitation, such as rate of neutralization, or concentration of the insulin analog or zinc or other additives, and this may affect the absorption of the insulin analog and hence rate of onset and duration of the resulting formulation following subcutaneous or intramuscular injection.

It will be apparent to those skilled in the art, enabled by the disclosure herein, that other formulations of the insulin analogs described herein may be obtained by modification of the above general procedures, leading to a broad range of formulations with varied rates of absorption following subcutaneous or intramuscular injection, and hence varied onsets and durations of action. It is also well known to those skilled in the art, that insulin molecules may be formulated in a manner such as to allow for delivery by non-parenteral routes, such as by oral, nasal, rectal, and conjunctival routes. The insulin molecules described in the application should also be suitably delivered in formulations where native insulins (e.g., human, bovine or porcine) have been delivered by these routes.

It should be understood that the effective amount of all or any of the insulin analogs administered to patients will be determined by the caregiver and will be based on criteria such as the size, age and sex of the patient, route of administration, as well as patient responsiveness and the degree to which the patient's pancreas fails to produce insulin. Patients can be started on dosing regimes similar to those which the patient was accustomed to with respect to insulin. Thereafter, the amount of the tissue-selective insulin analogs administered can be adjusted based on patient responsiveness.

EXPRESSION OF THE INSULIN FUSION PROTEIN

Insulin analogs are provided as fusion proteins expressed in bacterial cells. It is well known that many eucaryotic proteins are incapable of being expressed in bacterial cells in measurable amounts and are incapable of being expressed at commercially recoverable levels due to proteolysis of the foreign protein by the host. As described in copending, commonly assigned application Ser. No. 07/391,277, filed 8 August 1989 (published through the PCT as WO 90/01540 on 22 February 1990) and incorporated herein by reference, proteins which cannot be expressed in high yield may be expressed as a fusion protein to increase levels of expression. For purposes of the present invention, it is preferred that the insulin analogs be expressed as fusion protein with chloramphenicol acetyltransferase (CAT), which is a known selectable marker and an easily assayed enzyme for monitoring the efficiency of both eucaryotic and procaryotic expression (Delegeane, A. M., et al., Molecular Cell Biology (1987) 7:3994–4002). The fusion proteins which one begins with in the isolation and purification methods of the present invention are substantially of the same general type as described in the aforementioned patent application. The following is a brief summary of the fusion and expression process set forth in the aforementioned patent reference.

CAT encodes a 219 amino acid mature protein and the gene contains a number of convenient restriction endonuclease sites (5'-PvuII, EcoRI, DdeI, NcoI, and ScaI-3') throughout its length to test gene fusions for high level expression. These restriction sites may be used in constructing hybrid gene sequences.

Expression constructs using CAT can employ most of the CAT-encoding gene sequences or a substantially truncated portion of the sequence encoding an N-terminal portion of the CAT protein linked to the gene encoding the desired heterologous polypeptide. These expression constructs, which demonstrate enhanced levels of expression for a variety of heterologous proteins, utilize a number of varying lengths of the CAT proteins ranging in size from 73 to 210 amino acids. The 73 amino acid CAT fusion component is conveniently formed by digesting the CAT nucleotide sequence at the EcoRI restriction site. Similarly, the 210 amino acid CAT fusion component is formed by digesting the CAT nucleotide sequence with ScaI. These, as well as other CAT restriction fragments, may then be ligated to any nucleotide sequence encoding a desired protein to enhance expression of the desired protein.

The reading frame for translating the nucleotide sequence into a protein begins with a portion of the amino terminus of CAT, the length of which varies, continuing in-frame with or without a linker sequence into the proinsulin analog sequence, and terminating at the carboxy terminus thereof. An enzymatic or chemical cleavage site may be introduced downstream of the CAT sequence to permit ultimate recovery of the cleaved product from the hybrid protein. Suitable cleavage sequences and preferred cleavage conditions will be described below.

To avoid internal cleavage within the CAT sequence, amino acid substitutions can be made using conventional site-specific mutagenesis techniques (Zoller, M. J., and Smith, M., Nucl. Acids Res. (1982) 10:6487–6500, and Adelman, J. P., et al., DNA (1983) 2:183-193). This is conducted using a synthetic oligonucleotide primer complementary to a single-stranded phage DNA to be mutagenized except for limited mismatching, representing the desired mutation. These substitutions would only be performed when expression of CAT is not significantly affected. Where there are internal cysteine residues, these may be replaced to help reduce multimerization through disulfide bridges.

Procaryotic systems may be used to express the CAT fusion sequence; procaryotes most frequently are represented by various strains of *E. coli* (e.g., MC1061, DH1, RR1, W3110, MM294, MM294B, C600hf1, K803, HB101, JA221, and JM101), however, other microbial strains may also be used. Plasmid vectors which contain replication sites, selectable markers and control sequences derived from a species compatible with the host are used, for example, *E. coli* is typically transformed using derivatives of pBR322, a plasmid derived from an *E. coli* species by Bolivar et al., Gene (1977) 2:95. pBR322 contains genes for ampicillin and tetracycline resistance and thus provides multiple selectable markers which can be either retained or destroyed in construction of the desired vector.

In addition to the modifications described above which would facilitate cleavage and purification of the product polypeptide, the gene conferring tetracycline resistance may be restored to exemplified CAT fusion vectors for an alternative method of plasmid selection and maintenance.

Although the *E. coli* tryptophan promoter-operator sequences are preferred, different control sequences can be substituted for the trp regulatory sequences. Commonly used procaryotic control sequences which are defined herein to include promoters for transcription initiation, optionally with an operator, along with ribosome binding site sequence, include such commonly used promoters as the beta-lactamase (penicillinase) and lactose (lac) promoter systems (Chang et al., Nature (1977) 198:1056), the lambda-derived $P_L$ promoter (Shimatake et al., Nature (1981) 292:128) and N-gene ribosome binding site, and the trp-lac (trc) promoter system (Amann and Brosius, Gene (1985) 40:183).

Transformed microorganisms producing the fusion proteins are grown in a suitable growth medium containing compounds which fulfill the nutritional requirements of the microorganism. Growth media will typically contain assimilable sources of carbon and nitrogen, magnesium, potassium and sodium ions, and optionally, amino acids, purine and pyrimidine bases, vitamins, minerals, and the like.

At the end of fermentation, the bacterial paste is collected by, e.g., cross-flow filtration, centrifugation, or other conventional methods. The concentrated paste is preferably stored at a temperature below −20° C. preferably about −70° C., until further use.

Cell Disruption and Preparation of Inclusion Bodies

Following concentration of the bacterial paste, the cell membranes and cell walls of the microorganisms are disrupted, either chemically, i.e., with alkali or with a compound such as 1-octanol, enzymatically, e.g., with lysozyme, or mechanically, i.e., using a commercially available homogenizer or microfluidizer, as is well-known in the art. The end point of disruption can be monitored by microscopy and/or by adding a dye such as Coomassie Blue and monitoring its absorbance at 595 nm, which typically increases with cell lysis. This process step should be carried out for a time long enough to ensure that substantially all of the cells have been disrupted, and that substantially no intact cells will be carried through to subsequent process steps.

After cell disruption, the insoluble fraction of the whole-cell homogenate, containing inclusion bodies, is harvested by filtration, centrifugation, or the like. The inclusion body fraction is typically on the order of 10 to 30% of the initial wet-cell weight, and enrichment for the CAT/insulin analog fusion protein is thus desirable. To remove contaminating bacterial proteins, the inclusion body pellets are washed with a medium which contains 1 M guanidine hydrochloride together with dithiothreitol (DTT), e hylene diamine tetracetic acid (EDTA), and buffering agents. After washing, the inclusion bodies are pelleted by centrifugation and washed again with the aforementioned medium. This washing procedure is important to achieve relatively high (50–70%) yields of insulin analog. By washing away part of the contaminating bacterial protein, this procedure increases the proportion of inclusion body protein that is CAT-insulin analog fusion protein to about 50%. The inclusion bodies may, if desired, be frozen and stored.

CLEAVAGE OF THE FUSION PROTEIN

The reagent and methods used in cleaving the fusion proteins will depend on the cleavage sequence incorporated in the fusion protein at the outset. Cleavage sequences which may be used herein include, for example, those which cleave following methionine residues (cleavage reagent cyanogen bromide), glutamic acid residues (cleavage reagent endoproteinase Glu-C), tryptophan residues (cleavage reagent N-chlorosuccinimide with urea or with sodium dodecyl sulfate), and cleavage between asparagine and glycine residues (cleavage reagent hydroxylamine). For purposes of the present invention, cleavage with cyanogen bromide is particularly preferred.

The inclusion bodies obtained in the previous step, in solubilized form, are treated with the selected cleavage reagent at ambient temperature. The reaction is allowed to proceed for as long as necessary to ensure substantially complete cleavage of the fusion protein.

After the cleavage reaction is complete, the sample is dried. The dried cleavage mixture is subjected to sulfitolysis in order to modify the free sulfhydryl groups with S-sulfonates. The modified proinsulin analog in its stabilized S-sulfonate form is partially purified and can be refolded and converted to the active human insulin analog by known procedures. Refolding techniques allow the formation of the S—S bonds. The analog is folded to obtain the formation of disulfide bridges and converted to insulin. Finally, the insulin analog is purified by high pressure liquid chromatography (HPLC).

The invention is further illustrated by the following specific examples which are not intended in any way to limit the scope of the claimed invention. Specifics are given for construction of A12Gly insulin analogs, however, the procedure can be used to prepare other insulin analogs of the invention.

EXPERIMENTAL

The following examples are put forth so as to provide those of ordinary skill in the art with a complete disclosure and description of how to make, formulate and administer the insulin analogs and insulin analog pharmaceutical formulations of the invention, and are not intended to limit the scope of what the inventors regard as their invention. Efforts have been made to insure accuracy with respect to numbers used (e.g., amounts, temperatures, etc.), but some experimental errors and deviations should be allowed for. Unless indicated otherwise, parts are parts by weight, temperatures are in degrees centigrade, and pressure is at or near atmospheric.

Construction of Insulin Analogs

Insulin analogs are constructed my making nucleotide changes in the proinsulin cDNA molecule such that the resulting cDNA molecule encodes the desired amino acid substitution in the analog.

Proinsulin cDNA is constructed by combining a series of chemically synthesized oligonucleotides comprising a gene coding for human proinsulin and a linker sequence at the 5' end. The oligonucleotides, numbered 1–6 are described in FIG. 1 (SEQ ID NOS:1-6). The analogs are paired 1 with 2, 3 with 4, and 5 with 6. Each pair is phosphorylated, annealed and then ligated as follows. For the kinase reaction, 5 µg each of an oligonucleotide pair is brought to 100 µl in 70 mM Tris pH 7.6, 10 mM MgCl:, 5 mM DTT, 1 mM ATP and 20 units T4 polynucleotide kinase is added. The mixture is incubated at 37° C. for 1 hour and stopped by heating at 65° C. for 10 minutes. Oligonucleotides are annealed by heating the above samples to 100° C. for 3 minutes followed by a 30 minute incubation at room temperature and, then, incubating overnight at 4° C.

The pairs of annealed oligonucleotides are mixed (pooled and ligated by adding 10 mM ATP to bring the concentration to 1 mM in the presence of T4 DNA ligase. The samples are then incubated at 15° C. overnight. The ligated DNA is then digested with KpnI and HindIII and an approximately 280 bp fragment is gel purified by standard techniques.

The cDNA coding for proinsulin is inserted into plasmid vector pUC19 (Yannish-Perron, C., et al., Gene (1985) 33:103–119; Roberts, R. J., Nucl. Acids Res. (1987) 15 Suppl: r189–r217) is digested With KpnI and HindIII by standard techniques. The resulting vector is designated pPINS. The vector containing the proinsulin DNA (pPINS) is digested with EcoRI and NdeI and ligated with a DNA fragment coding for amino acids 1–73 of CAT that is digested with NdeI and EcoRI. The resulting plasmid will contain DNA sequences which code for amino acids 1–73 of CAT, an 8 amino acid linker sequence (FIG. 2a), and human proinsulin. This plasmid, pUC-CAT-proinsulin, is used to construct cDNAs for insulin analogs.

Insulin analogs were constructed using a repetitive series of enzymatically catalyzed polymerization reactions using an automated thermal cycler (Perkin Elmer Cetus DNA Thermal Cycler). The construction of A12Gly is illustrated below. Two oligonucleotide primers were utilized. One primer was complementary to the antisense strand at the end of the cDNA and has the following sequence (SEQ ID NO:9): 5'-CCG GAA TTC GAG CTC GGT ACC CGG-3'. The other primer was complementary to the sense strand at the 3' end of the cDNA except for the nucleotide codon which codes for the desired amino acid change. To construct the A12Gly analog, the oligonucleotide primer complementary to the sense strand, 5'-GCC AAG CTT CTA GTT GCA GTA GTT CTC CAG CTG GTA GAG ACC GCA-3' (SEQ ID NO:10), was used. This primer codes for amino acid Gly at position number 12 rather than amino acid Ser found in proinsulin. A19His is constructed in the same manner except that the primer complementary to the sense strand contains the sequence 5'-GCC AAG CTT CTA GTT GCA ATG GTT TTC-3' (SEQ ID NO:11) and codes for amino acid His at position 19 rather than the amino acid Tyr found in proinsulin. By using polymerase chain reaction technology (PCR), the desired DNA sequence coding for the amino acid (Gly) is substituted for the naturally occurring amino acid (Ser) at this position. The DNA sequence coding for proinsulin is shown in FIG. 2 and SEQ ID NO:7. For the polymerase chain reaction, the mixture was as follows: 10 μl 10×PCR buffer (500 mM KCl, 100 mM Tris-HCl pH8.3), 16 μl 1.25 mM deoxynucleotide mix (dATP, dGTP, dTTP, dCTP), 1 μM oligonucleotide primers, 1 ng template pUC-CAT-proinsulin, 10 μl 100% DMSO, 0.5 μl (2.5 units) Taq polymerase, and $H_2O$ to a final volume of 100 μl. The reaction mix was overlaid with a few drops of mineral oil and then the cycler was programmed to repeat the following cycle:
1. Denature at 94° C. for 1 minute;
2. Anneal at 55° C. for 30 seconds;
3. DNA synthesis at 72° C. for 30 seconds.

The amplification reaction was carried out for 30 cycles.

The PCR reaction mixture was then extracted once with phenol:chloroform:isoamyl alcohol (25:24:1) and once with chloroform:isoamyl alcohol (24:1). Sodium acetate (1/10 volume of 3M) and 2 volumes of 100% ethanol were added and the sample incubated for a minimum of 15 minutes at −70° C. The precipitated DNA was collected by centrifugation in a microfuge for 15 minutes at 4° C. The dry pellet was resuspended in 45 μl $H_2O$ and digested with KpnI and HindIII by adding 5 μl 10×KpnI buffer (100 mM NaCl, 100 mM Tris-Cl pH 7.5, 100 mM $MgCl_2$, 10 mM DTT), 40 units KpnI, and 40 units HindIII. The approximately 280 bp DNA fragment was purified by electrophoresis on an agarose gel and extracted from the gel. The purified fragment was then inserted by ligation into the expression vector pTrp233 (U.S. Pat. No. 4,764,504) containing CAT. The expression vector was digested with KpnI and HindIII. For the ligation mixture, 2.5 μl 10×ligase buffer (0.5 M Tris-Cl pH 7.4, 0–1M $MgCl_2$, 0.1 M DTT), 2.5 μl 10 mM ATP, 20 ng of the digested expression vector, 2.5 ng PCR DNA fragment, and 1 μl T4 DNA ligase (NE Biolabs) was mixed with water to a final volume of 25 μl.

The ligation reaction was allowed to proceed for 2 hours at room temperature and then used to transform competent E. coli cells by standard techniques as described in detail below. From the transformed cells, a single colony was isolated and used to prepare plasmid. This plasmid was subjected to DNA sequencing by standard techniques to ensure that the desired cDNA coding for the insulin analog A12Gly (SEQ ID NOS:12 and 13) was used to transform the cells to be used as a source for the production of recombinant insulin analog.

Production, Isolation and Purification of Recombinant Insulin Analogs

Expression

The human insulin analogs A12Gly (SEQ ID NOS:12 and 13) and A19His (SEQ ID NOS:14 and 15) were expressed as fusion proteins with portions of the bacterial CAT protein in E. coli. These methods are routinely used to purify insulin analogs expressed as a CAT fusion protein in E. coli. For purposes of this example, expression of insulin analogs A12Gly or A19His will be described.

The insulin analog described above was joined to the carboxy terminus of the CAT sequence through a cyanogen bromide susceptible methionine linkage. The CAT-insulin analog fusion was expressed from the tryptophan promoter of the bacterial expression vector pTrp233.

The plasmid was used to transform E. coli W3110 (ATCC Accession No. 27325) and selected for ampicillin resistance. Transformants were grown in culture overnight at 37° C. in complete M9 medium containing M9 salts, 2 mM $MgSO_4$, 0.1 mM $CaCl_2$, 0.4% glucose, 0.5% casmaino acids, 40 μg/ml tryptophan, 2 μg/ml thiamine hydrochloride, and 100 μg/ml ampicillin sulfate. The overniqht culture (45–50 ml) was used to inoculate 2 L of M9 medium containing 4–8 μg/ml tryptophan. Fusion protein expression was induced using 25 μg/ml indole acrylic acid by standard methods when the cells reached an $OD_{590}$ of 0.4–0.5. Cells were allowed to continue to grow for 4–5 hours at 37° C. Bacterial paste was collected by centrifugation and stored at −20° C. until use.

Preparation of Inclusion Bodies

A model W-225R sonicator (Heat Systems Ultrasonics, Inc., Plainview, N.Y.) was used to disrupt about 8 g of cells. Cells were suspended in 45 ml TE buffer (10 mM Tris pH 7.5, 1 mM EDTA), 1 mM DTT, on ice. The sonicator was set at 7, constant duty cycle. The blunt tip was used for 2 times, 2 minutes with a one minute cooling interval. Samples of homogenate were monitored for cell lysis by microscopy. Ten ml of 6 M guanidine-HCl solution was added to a final concentration of 1 M in 60 ml to improve washing of the inclusion bodies. Up to 200 ml of buffer (TE/DTT/guanidine-HCl) were added to further improve the wash. Washed inclusion bodies were pelleted by centrifugation at 5000–7000 rpm for 10 minutes in a RC-B GSA rotor, and resuspended in 20 ml of TE/DTT/guanidine-HCl. The undissolved fraction of the whole cell homogenate, containing inclusion bodies, was harvested by centrifugation at 5000 X rpm in an SS-34 rotor for 15 minutes. The pellet, containing CAT proinsulin analog fusion protein was stored at −20° C. or subjected to cyanogen bromide (CNBr) cleavage.

CNBr Cleavage of Fusion Protein

CAT73/proinsulin analog fusion protein was cleaved with CNBr. Inclusion bodies (about 2–3 g) were resuspended in 3 ml of deionized water and then added dropwise to 16 ml of 88% formic acid. CNBr (120 mg) was added to solubilized inclusion bodies, the sample was sealed under argon or nitrogen, and then gently stirred at room temperature for 4 hours. The sample was allowed to dry overnight and the dried residue was stored at −20° C. in a desiccator.

Sulfitolysis

The dried cleavage mixture was redissolved in 12 ml of sulfitolysis buffer (6 M guanidine-HCl, 50 mM ammonium bicarbonate) and the pH adjusted to 9.0 with ethanolamine (100–200 μl). Two hundred milligrams of sodium sulfite and 100 mg of sodium tetrathionate were added while stirring, and the pH was readjusted to 9.0 with ethanolamine. The reaction mixture was stirred at room temperature for 6 hours to convert cysteines and cystines to s-sulfonate groups. The reaction was terminated by addition of 1/20 volume of 1 M HEPES and about 0.4 ml of 2 N HCl to pH 7 and stored overnight at −2° C.

The reaction mixture was desalted on a Sephadex G-15 column in 7 M urea, 20 mM Tris pH 7.5. The desalted protein was loaded on a DEAE Sepharose Fast Flow column and washed with 7 M urea, 20 mM Tris pH 7.5 followed by 50 mM NaCl, 7 m urea, 20 mM Tris pH 7.5. The column was eluted with a 200 ml linear gradient of 50–250 mM NaCl using a GM-3 gradient maker (Pharmacia). The proinsulin-analog sulfonate fractions were identified by UV trace at 226 nm and/or migration on SDS-PAGE.

Refolding

DEAE fraction pool containing the proinsulin-analog sulfonate was desalted on a G-15 column, equilibrated with 50 mM glycine buffer, pH 10, and the appropriate fractions, identified by absorbance at 226 nm and were pooled. The Pierce BCA Protein Assay (Pierce, Rockford, Ill.) using Bicinchoninic Acid A was run on the glycine desalted pool of proinsulin analog sulfonate.

The proinsulin analogs were induced to fold with the correct formation of intramolecular disulfide bonds by controlled sulfhydryl interchange catalyzed by $\beta$-mercaptoethanol. Proinsulin analog glycine pool fractions were diluted with degassed glycine buffer, pH 10 to a concentration of 0.1–0.4 mg/ml and then 0.01 volume of 60 mM $\beta$-mercaptoethanol reagent was slowly added. The sample was blanket sealed under argon, incubated at 4° C., overnight, and protected from the light.

Enzymatic Transformation

The sample was transformed enzymatically, generally as described in European Patent Application No. 0 264 250, which is incorporated herein by reference. The refolded sample was concentrated to approximately 2 mg/ml. To the proinsulin-analog concentrate in 50 mm glycine buffer pH 10 was added 1 M HEPES (to a final concentration of 10 mM), 2 N HCl (to adjust the refold solution to pH 7.2–7.5), 200 mM $CaCl_2$ (final concentration 2.0 mM), and 10 mM $NiCl_2$ (to a final concentration of 0.1mM). Carboxypeptidase B (Worthington, 186 units/mg) at 0.4 mg/ml in 10 mM HEPES, pH 7.5 was added to a final concentration of 4 $\mu$g/ml. Trypsin-TPCK (Worthington, 225 units/mg) at 0.1 mg/ml, in 10 mM HEPES pH 7.5) was added (final concentration 1 $\mu$g/ml). The sample was incubated at 5° C. to −12° C. Conversion was monitored by reversed phase HPLC and completed within 5 to 17 hours. Enzymatic transformation was terminated by addition of 2.5 M acetic acid/ammonium acetate pH 3.5 to a final concentration of 0.25 M and stored at 5° C. Acetonitrile (10% v/v) was added to samples to be analyzed by HPLC and to inhibit microbial growth.

Analysis of Refold and Enzymatic Transformation

Refolded samples were analyzed after concentration to determine if proper folding had occurred. Samples (100 $\mu$l) for analysis were prepared by dilution with 100 $\mu$l of 0.5 m acetic acid and 200 $\mu$l of equilibration mobile phase (20% acetonitrile/0.25 M acetic acid/ammonium acetate pH 3.5, followed by mixing and centrifugation to clarify. A 200–400 $\mu$l sample was loaded through a loop/injector onto a Toso-Haas TSK ODS 120T 5um analytical column, 250×4.6 mm with direct connect guard column and packed with Vydac pellicular media (Vydac, Hesperia, Calif.). Equilibration was with 20% acetonitrile in 0.25 M acetic acid/ammonium acetate pH 3.5. Samples were eluted with a linear gradient of 25–40% acetonitrile at 0.5% per minute. The UV absorbance of the column effluent was monitored at 276 nm. This chromatography system was also used to examine the sample after enzymatic transformation. In this analysis, the enzymatically transformed species ran earlier than the proinsulin-analog demonstrating the conversion of the proinsulin analog to the insulin analog. This analysis also provided a basis for designing the preparative HPLC purification of the insulin analog.

HPLC Purification of the Transformed Analog

After enzymatic digestion, the clarified solution was purified on a C18 reversed phase high pressure liquid chromatography column (RP-HPLC). The column was a TSK ODS 120T 10 $\mu$300×7.8 mm column. Up to 30 mg of total protein was loaded per run by multiple injections through a 5 ml loop. After the sample was loaded, the column was equilibrated with 0.25 M acetic acid/ammonium acetate pH 3.5/20% acetonitrile and then eluted with an acetonitrile gradient from 20% to 50%. The insulin analog usually eluted between 28% to 30% acetonitrile. The appropriate peak was identified by absorbance at 276 nm and collected. Purified analog fractions were pooled and protein concentration determined. The pooled sample was quick frozen and lyophilized.

For identification and verification of each purified insulin analog, 1–20 $\mu$g samples were analyzed for peptide sequence and amino acid composition. A 5–10 $\mu$g sample was analyzed by HPLC to assess purity. A Vydac 218TP5415 column was equilibrated in 90% Buffer A/10% Buffer B. (Buffer A is 0.075% TFA (trifluoroacetic acid) in water; Buffer B is 0.05% TFA/100% acetonitrile) A linear gradient from 10% to 40% buffer B over 30 minutes was run at 1.0 ml/min., and the column effluent monitored at 215 nm. The samples were approximately 85–95% pure.

In Vivo Methods

The in vivo studies were designed to assess the potency of insulin analogs and to determine if analogs have a tissue selectivity different from insulin.

Analogs were tested using the euglycemic, hyperinsulinemic clamp method. In this study, different rates of insulin analog were infused concurrently with variable rates of glucose. The exogenous glucose was infused at a rate sufficient to maintain euglycemia for the duration of the experiment. Additionally, [D-3-$^3$H]glucose (tracer) is infused to assess glucose metabolism (i.e, glucose turnover). The steady state equation of Steele et al. (*Am. J. Physiol.* (1956) 187:15–241) Was used to calculate hepatic glucose output and the rate of glucose disposal. Under steady state conditions, glucose (mg/ml) and $^3$H-glucose (dpm/ml) levels are constant. Under these conditions the rate of glucose appearance ($R_a$)=rate of glucose disappearance ($R_d$). At steady state $R_a = R_d$. $R_a$ is further defined as the rate of glucose entering the glucose pool (approximately the blood volume and other extra-cellular volume). $R_a$ is equal to the rate at which the liver is making glucose plus the rate of any exogenous glucose infusion. $R_d$ is equal to the rate of glucose leaving the pool.

Three main parameters are used to assess the effects of the analogs. The rate of exogenous infusion (i.e., glucose infusion rate, GIR or M) estimates the potency of analog. $R_d$ indicates the degree, relative to insulin, to which an analog acts at peripheral tissues. Finally, hepatic glucose output (HGO), reflects the ability of the analogs to suppress the liver's production of glucose. HGO is calculated as $R_a$ minus M. To be hepatoselective, the decrease in HGO will be greater than the stimulation of $R_d$ compared to that observed with insulin.

Four to five days prior to experimentation, 65 mg/kg of sodium pentobarbital was administered intraperitoneally to anesthetize rats. Catheters were inserted in the right jugular vein and left carotid artery. The catheters were routed subcutaneously to the dorsal region of the neck and exteriorized. Following the recovery period, insulin or insulin analog plus glucose tracer were infused into the carotid artery. Blood samples were taken from the jugular vein. After collecting basal sample, as described below, insulin or analog infusion was started. At 10 minute intervals after starting hormone infusion, 50 μl blood samples were taken to determine the plasma glucose level. During infusion of hormone, a 30% glucose solution was infused at an empirically determined rate to maintain the basal glucose level.

A bolus of 4 μCi 3-$^3$H-glucose solution followed by a continuous infusion of a 10 μCi/ml solution of 3-$^3$H-glucose at a rate of 20 ml/min (effective dose 0.2 μCi/min) starting 120 minutes before the insulin and cold glucose infusion and continuing throughout the clamp was made. Insulin or analog infusion was started at time 0. Aliquots of whole blood were obtained at −20, −10 and 0 minutes before the clamp was started, and later at 70, 80, and 90 minutes into the clamp and the plasma glucose level determined. Glucose specific activity at these times was also determined as follows:

$$\text{Glucose specific activity} = \frac{\text{dpm } ^3\text{H-glucose}}{\text{mg glucose}}$$

The blood was deproteinized with 10% TCA, centrifuged, and an aliquot of supernatant dried in a vacuum oven to evaporate off $^3$H$_2$O. The $^3$H-glucose levels in the sample were determined using a liquid scintillation counter. Basal $R_a$ (glucose appearance rate) and clamp $R_a$ were calculated by using steady state glucose specific activity (basal: −20, −10 and ? minutes; clamp: 70, 80, 90 minutes) and the following equation:

$$R_a = \frac{^3\text{H-glucose infusion rate (dpm/min)}}{\text{Steady state glucose specific activity (dpm/mg)}}$$

Under basal conditions, at steady state, $R_a = R_d$ and $R_a$ hepatic glucose output. Under clamp conditions, at a steady state, $R_a = R_d$, however under these conditions, $R_a$ = hepatic glucose output plus exogenous glucose infusion rate. Hepatic glucose output under clamp conditions was determined by subtracting the glucose infusion rate from the calculated $R_d$.

In Vivo Results

A summary of the in vivo data is found in Table I.

A12Gly

Figure 3B:
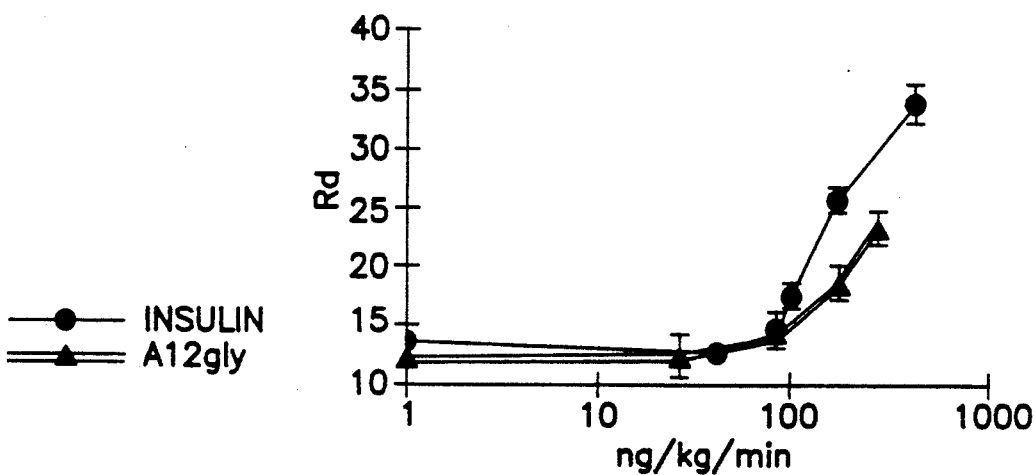
Figure 3C:
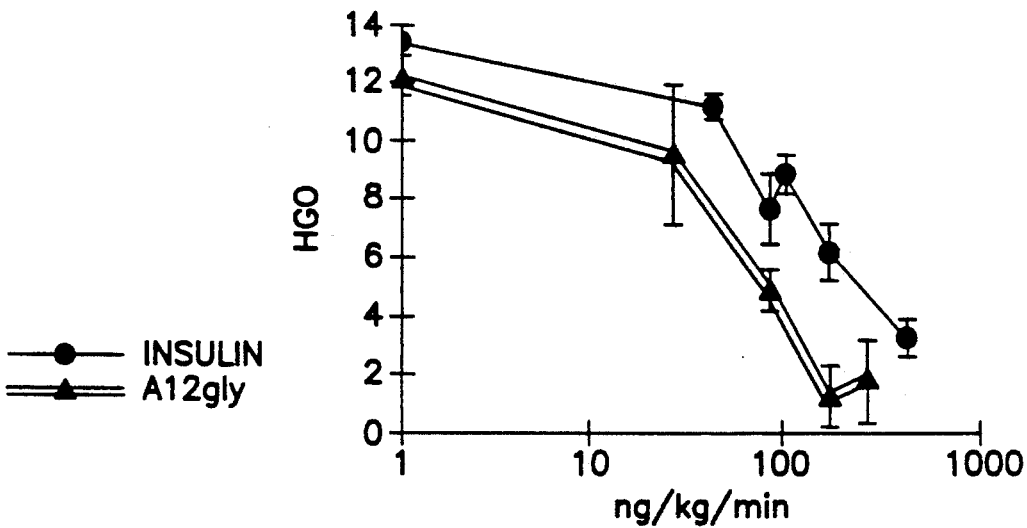

A12Gly insulin analog was tested in animals at 25.5, 83.0, 166, and 255 ng/kg/min. When A12gly was infused at 25.5 ng/kg/min, the $R_d$ was 12.8 mg/kg/min and HGO was 9.7 mg/kg/min (FIG. 3 and Table I). This represents little, if any, stimulation of $R_d$ (1.03 fold) and a 22% suppression of HGO. At the 83 ng/kg/min dose, $R_d$ was 14.4 mg/kg/min (1.16 fold stimulation) and HGO was 5.2 mg/kg/min (58% suppression). At the 166 and 255 ng/kg/min doses, $R_d$ was 19.1 and 23.8 mg/kg/min, respectively, and HGO was 1.5 and 2.1 mg/kg/min, respectively. This is equivalent to a 1.5 and 1.9 fold stimulation of $R_d$ and an 88% and 83% suppression of HGO for these two doses. From these data, it appears that A12Gly is more potent than insulin at the liver and slightly less potent than insulin at the periphery. A12Gly has approximately 1.9 the potency of insulin in suppressing HGO and 0.75 the potency of insulin in stimulating $R_d$ indicating that A12Gly is hepatoselective. The ratio of in vivo liver to peripheral activity is approximately 2.6.

A19His

Figure 4A:
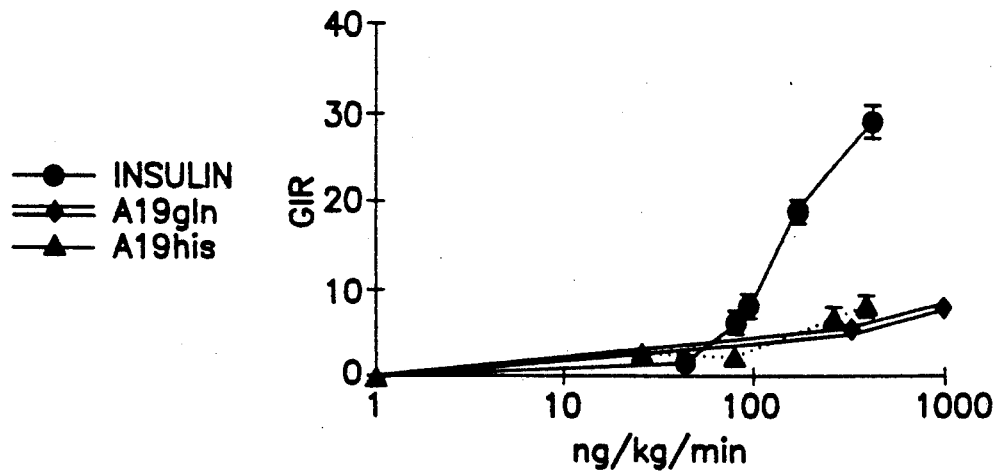
FIG. 4 shows glucose turnover for insulin, the A19Gln analog and the A19His analog. Graph A shows the rate of exogenous glucose infusion. Graph B shows the rate of glucose disappearance ($R_d$). Graph C shows the hepatic glucose output (HGO) and is calculated as $R_a$ minus GIR.
Figure 4B:
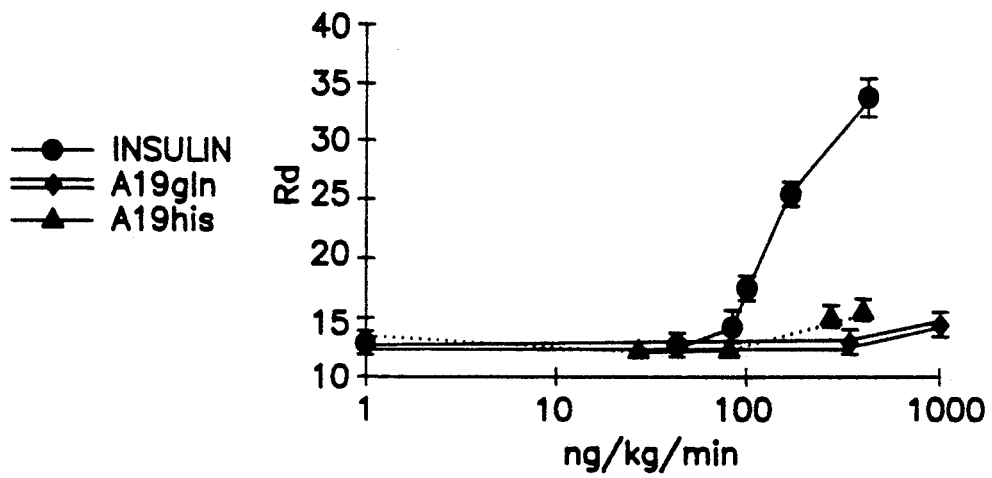
Figure 4C:
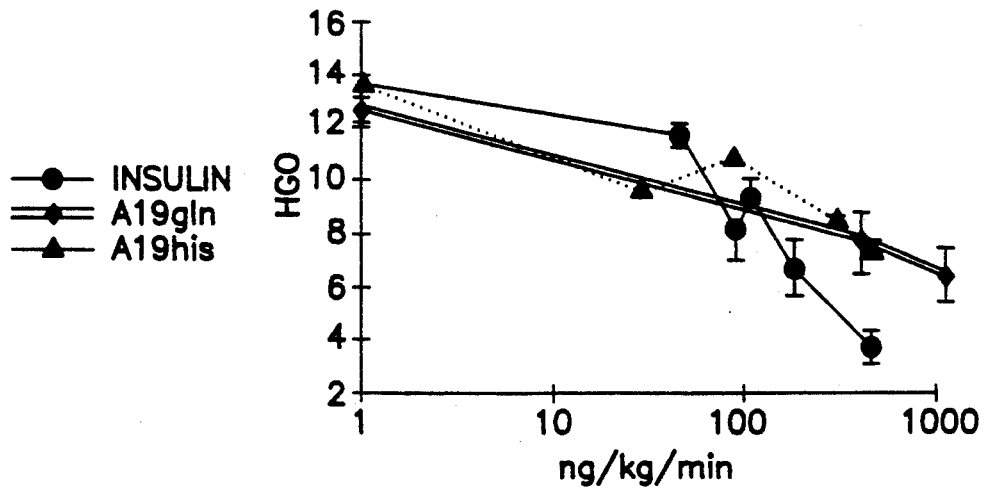

The analog was tested at 25.5, 76.5, 255, and 373 ng/kg/min doses. Results of the studies with A19His and insulin are shown in FIG. 4 and Table I. The glucose infusion rates necessary to maintain euglycemia at the 25.5 and 76.5 ng/kg/min doses of A19His were very low (3.1 and 2.0 mg/kg/min, respectively). Because of this result, the analog was infused at higher doses. At the 255 ng/kg/min dose, $R_d$ was 15.7 mg/kg/min (1.16 fold stimulation) and HGO was 7.4 mg/kg/min (45% suppression). At the 373 ng/kg/min dose, $R_d$ was 16.0 mg/kg/min (1.19-fold stimulation) and HGO was 7.2 mg/kg/min (47% suppression). These results indicate that when HGO is inhibited by approximately 50%, there is very little stimulation of $R_d$. By comparing the data for A19His to that for insulin, it can be seen that the potency of A19His is less than that for insulin. However, the potency of A19His in suppressing HGO (approximately 0.3) is greater than its potency in stimulating $R_d$. To determine the peripheral potency ($R_d$) and the in vivo ratio of hepatic activity to peripheral activity from these data, it was necessary to extrapolate the $R_d$ curve. We estimate the peripheral potency to be approximately 0.10 and the ratio to be approximately 3. These results indicate that A19His is hepatoselective in vivo.

A12Gly/A19His

A12Gly/A19His, prepared in a similar manner to the analogs described above, contains two substitutions in one molecule which have been shown to be hepatoselective individually. Animals were tested at 100 ng/kg/min, 333 ng/kg/min, and 1000 ng/kg/min. At the 100 ng/kg/min dose, $R_d$ was 14.5 mg/kg/min (1.1-fold simulation) and HGO was 8.3 mg/kg/min (36% suppression). At the 333 ng/kg/min dose, $R_d$ was 16.7 mg/kg/min (1.3-fold stimulation) and HGO was 217 mg/kg/min (79% suppression). At a dose of 1000 ng/kg/min, $R_d$ is stimulated by 2.0-fold and HGO is suppressed by 80% (Table I). These results suggest that A12gly/A19his is hepatoselective (Table I). When compared to the animals treated with A19His, A12-Gly/A19His is similar to A19His in stimulating $R_d$ and is more potent in suppressing HGO than is A19His. A12Gly/A19His appears to be 4-fold hepatoselective.

A19Gln

A19Gln, prepared in a similar manner to the analogs described above, was tested at 333 and 1000 ng/kg/min doses (FIG. 4 and Table I). At the 333 ng/kg/min dose, $R_d$ was 13.3 mg/kg/min (1.1-fold stimulation) and HGO was 7.4 mg/kg/min (40% suppression). At the 1000 ng/kg/min dose, $R_d$ was 14.7 (1.2-fold stimulation) and HGO was 6.1 (51% suppression). The in vivo data are similar to the results obtained with A19His and indicate that A19Gln is hepatoselective.

A14Phe and A10Pro/A13Trp

Each analog, prepared in a similar manner to the analogs described above, was infused at 100 and 333 ng/kg/min. $R_d$ was stimulated to approximately the same extent by each analog and found to be similar to insulin stimulation (Table I). Both analogs were less effective suppressing HGO than was insulin indicating that they are peripheral selective.

A14Gly

A14Gly Was tested at 41.5, 100, 333, and 415 ng/kg/min. At the 41.5 ng/kg/min dose, $R_d$ was 13.8 mg/kg/min (1.1 fold stimulation) and HGO was 12.3 mg/kg/min (6% suppression). At the 100 ng/kg/min dose, $R_d$ was 16.3 mg/kg/min (1.4 fold stimulation) and HGO was 5.5 mg/kg/min (55% suppression). At the 333 ng/kg/min dose, $R_d$ was 21.7 mg/kg/min (1.7 fold stimulation) and HGO was 2.5 mg/kg/min (82% suppression). At the 415 ng/kg/min dose, $R_d$ was 22.2 mg/kg/min (1.6 fold stimulation) and HGO was 5.7 mg/kg/min (60% suppression) (Table I). These results indicate that A14Gly is hepatoselective in vivo.

A12Thr

A12Thr was tested at 100 and 333 ng/kg/min. At the 100 ng/kg/min dose, $R_d$ was 20.1 ng/kg/min (1.6 fold stimulation) and HGO was 9.6 mg/kg/min (24% suppression). At the 333 ng/kg/min dose, $R_d$ was 39.2 ng/kg/min (3.1 fold stimulation) and HGO was 3.4 mg/kg/min (69% suppression). These results indicate that A12Thr is peripheral selective.

TABLE I
SUMMARY OF IN VIVO DATA

| Analog | $R_d$ mg/kg/min | HGO mg/kg/min | GIR mg/kg/min |
|---|---|---|---|
| Insulin | | | |
| basal | 13.5 ± 0.4 | 13.5 ± 0.4 | 0 |
| 41.5 | 13.0 ± 0.3 | 11.3 ± 0.3 | 1.7 ± 0.6 |
| 83 | 14.7 ± 1.3 | 7.8 ± 1.1 | 6.9 ± 0.8 |
| 100 | 17.8 ± 1.0 | 9.1 ± 0.7 | 8.8 ± 1.2 |
| 166 | 26.1 ± 0.8 | 6.4 ± 1.1 | 19.7 ± 0.5 |
| 415 | 34.3 ± 1.6 | 3.5 ± 0.7 | 30.8 ± 1.7 |
| Human A12Gly | | | |
| basal | 12.4 ± 0.68 | 12.4 ± 0.68 | 0 |
| 25.5 | 12.8 ± 2.1 | 9.7 ± 2.4 | 3.0 ± 0.8 |
| 83.0 | 14.4 ± 0.8 | 5.2 ± 0.4 | 9.2 ± 1.2 |
| 166 | 19.1 ± 1.4 | 1.5 ± 1.1 | 17.7 ± 2.2 |
| 255 | 23.8 ± 1.4 | 2.1 ± 1.4 | 21.7 ± 1.3 |
| Human A19His | | | |
| basal | 13.5 ± 0.8 | 13.5 ± 0.8 | 0 |
| 25.5 | 12.5 | 9.4 | 3.1 |
| 76.5 | 12.6 | 10.6 | 2.0 |
| 255 | 15.7 ± 0.6 | 7.4 ± 0.9 | 8.3 ± 1.2 |
| 373 | 16.0 ± 0.7 | 7.2 ± 0.4 | 8.8 ± 0.9 |
| Human A19Gln | | | |
| basal | 12.5 ± 0.7 | 12.5 ± 0.7 | 0 |
| 333 | 13.1 ± 1.0 | 7.4 ± 1.1 | 5.8 ± 0.3 |
| 1000 | 14.7 ± 0.9 | 6.1 ± 1.0 | 8.6 ± 0.6 |
| Human A12Gly/A19His | | | |
| basal | 13.0 ± 0.4 | 13.0 ± 0.4 | 0 |
| 100 | 14.5 ± 0.6 | 8.3 ± 1.0 | 6.1 ± 1.0 |
| 333 | 16.7 ± 1.8 | 1.7 ± 0.6 | 14.0 ± 2.0 |
| 1000 | 26.4 ± 2.6 | 3.1 ± 1.1 | 23.4 ± 1.6 |
| Human A14Phe | | | |
| basal | 15.5 ± 0.6 | 15.5 ± 0.6 | 0 |
| 100 | 21.2 ± 0.9 | 12.9 ± 1.4 | 8.4 ± 2.3 |
| 333 | 32.3 ± 4.0 | 6.2 ± 2.6 | 26.1 ± 2.9 |
| Human A10Pro/A13Trp | | | |
| basal | 12.7 ± 1.2 | 12.7 ± 1.2 | 0 |
| 100 | 18.8 ± 1.9 | 10.2 ± 1.8 | 8.5 ± 0.5 |
| 333 | 31.3 ± 1.9 | 8.9 ± 2.7 | 22.4 ± 1.9 |
| Human A12Ala | | | |
| basal | 13.6 ± 0.9 | 13.6 ± 0.9 | 0 |
| 100 | 19.3 ± 1.3 | 9.7 ± 1.3 | 9.6 ± 0.4 |
| 333 | 29.1 ± 2.7 | 6.1 ± 0.9 | 22.9 ± 3.1 |
| 1000 | 48.6 ± 2.1 | 6.2 ± 0.5 | 42.4 ± 2.2 |
| Analog | $R_d$ mg/kg/min | HGO mg/kg/min | M mg/kg/min |
| A14Gly | | | |
| basal | 13.2 ± 0.6 | 13.2 ± 0.6 | 0 |
| 41.5 | 13.8 ± 1.1 | 12.3 ± 0.8 | 1.6 ± 0.5 |
| 100 | 16.3 ± 0.8 | 5.5 ± 1.2 | 10.8 ± 1.0 |
| 333 | 21.7 ± 1.5 | 2.5 ± 1.1 | 19.5 ± 2.2 |
| 415 | 22.2 ± 1.0 | 5.7 ± 0.9 | 16.5 ± 1.7 |
| A12Thr | | | |
| basal | 12.7 ± 0.4 | 12.7 ± 0.4 | 0 |
| 100 | 20.1 ± 0.8 | 9.6 ± 1.2 | 10.5 ± 0.6 |
| 333 | 39.2 ± 1.5 | 3.4 ± 1.1 | 35.9 ± 1.6 |

The instant invention as shown and described herein was considered to be the most practical and preferred embodiment. It is recognized, however, that departures may be made therefrom which are within the scope of the invention, and that obvious modifications will occur to one skilled in the art upon reading this disclosure.

We claim:

1. A human insulin analog wherein position A12$_{Ser}$ is substituted with Gly and the analog is hepatoselective.

2. A human insulin analog wherein position A12$_{Ser}$ is substituted with Thr and the analog is peripherally selective.

3. A human insulin analog comprising a hydrophilic amino acid substitution at position A19$_{Tyr}$, where the analog is hepatoselective.

4. The insulin analog of claim 3, wherein position A19$_{Tyr}$ is substituted by either His or Gln.

5. A human insulin analog comprising amino acid substitutions at both positions A12$_{Ser}$ and A19$_{Tyr}$, wherein position A12$_{Ser}$ is substituted with Gly and A19$_{Tyr}$ is substituted with His and the analog is hepatoselective.

6. A human insulin analog comprising a hydrophobic amino acid substitution at position A14$_{Tyr}$, wherein the analog is peripherally selective.

7. The insulation analog of claim 6, wherein position A14$_{Tyr}$ is substituted with Phe.

8. A human insulin analog comprising a hydrophilic amino acid substitution at position A14$_{Tyr}$, wherein the analog is hepatoselective.

9. The insulin analog of claim 8, wherein position A14$_{Tyr}$ is substituted with Gly.

10. A human insulin analog comprising amino acid substitutions at both positions A12$_{Ser}$ and A14$_{Tyr}$, wherein position A12$_{Ser}$ is substituted with Thr and position A14$_{Tyr}$ is substituted with Gly and the analog is hepatoselective.

11. A human insulin analog comprising hydrophobic amino acid substitutions at both positions A10$_{Val}$ and A13$_{Leu}$, wherein the analog is peripherally selective.

12. The insulin analog of claim 11, wherein position A10$_{Val}$ is substituted with Pro and position A13$_{Leu}$ is substituted with Trp.

* * * * *